United States Patent
Shimada et al.

(10) Patent No.: US 9,198,628 B2
(45) Date of Patent: Dec. 1, 2015

(54) CHEST DIAGNOSTIC SUPPORT INFORMATION GENERATION SYSTEM

(75) Inventors: Tetsuo Shimada, Hino (JP); Shintaro Muraoka, Hachioji (JP); Sho Noji, Tachikawa (JP)

(73) Assignee: KONICA MINOLTA, INC. (JP)

( * ) Notice: Subject to any disclaimer, the term of this patent is extended or adjusted under 35 U.S.C. 154(b) by 769 days.

(21) Appl. No.: 13/476,116

(22) Filed: May 21, 2012

(65) Prior Publication Data

US 2012/0300904 A1 Nov. 29, 2012

(30) Foreign Application Priority Data

May 24, 2011 (JP) .................. 2011-115601

(51) Int. Cl.
*A61B 6/00* (2006.01)
*G06T 7/00* (2006.01)

(52) U.S. Cl.
CPC .............. *A61B 6/4291* (2013.01); *A61B 6/4405* (2013.01); *A61B 6/463* (2013.01); *A61B 6/486* (2013.01); *A61B 6/507* (2013.01); *A61B 6/5217* (2013.01); *A61B 6/5235* (2013.01); *A61B 6/542* (2013.01); *G06T 7/0016* (2013.01); *A61B 6/468* (2013.01); *A61B 6/5205* (2013.01); *A61B 6/5258* (2013.01); *G06T 2207/10016* (2013.01); *G06T 2207/10116* (2013.01); *G06T 2207/30061* (2013.01)

(58) Field of Classification Search
CPC ...... A61B 6/486; A61B 6/507; A61B 6/5205; A61B 6/5217; G06T 2207/30061; G06T 7/0016
USPC ............................................ 378/62; 382/131
See application file for complete search history.

(56) References Cited

U.S. PATENT DOCUMENTS

2005/0243967 A1* 11/2005 Inoue .............................. 378/97

FOREIGN PATENT DOCUMENTS

JP 2006-68512 A 3/2006
JP 2009-136573 A 6/2009

(Continued)

OTHER PUBLICATIONS

Machine translation of Japanese patent document No. JP2010-268979A.*

(Continued)

*Primary Examiner* — David J Makiya
*Assistant Examiner* — John Corbett
(74) *Attorney, Agent, or Firm* — Cantor Colburn LLP

(57) ABSTRACT

A chest diagnostic support information generation system includes: a radiography section which radiographs a chest portion of a subject; an image analysis section which generates a diagnostic support information based on an image data generated by the radiography section; and a display which displays the diagnostic support information, wherein the radiography section obtains a plurality of frame images which show a motion state of the chest of the subject, and the image analysis section includes: a breathing information generation section which generates the diagnostic support information relating to breathing of the subject based on a difference value of the pixel or the block corresponded with each other between image frames temporally adjacent among the plurality of frame images; and a blood flow information generation section which generates the diagnostic support information relating to blood flow of the subject based on a generated output signal wave form.

10 Claims, 25 Drawing Sheets

(56) References Cited

FOREIGN PATENT DOCUMENTS

| | | | |
|---|---|---|---|
| JP | 2010-268979 A | | 12/2010 |
| JP | 2010268979 A | * | 12/2010 |
| WO | 2009/090894 A1 | | 7/2009 |

OTHER PUBLICATIONS

Japanese Office Action corresponding to Patent Application No. 2011-115601; Date of Mailing: Sep. 24, 2014, with English translation.

* cited by examiner

FIG. 12A
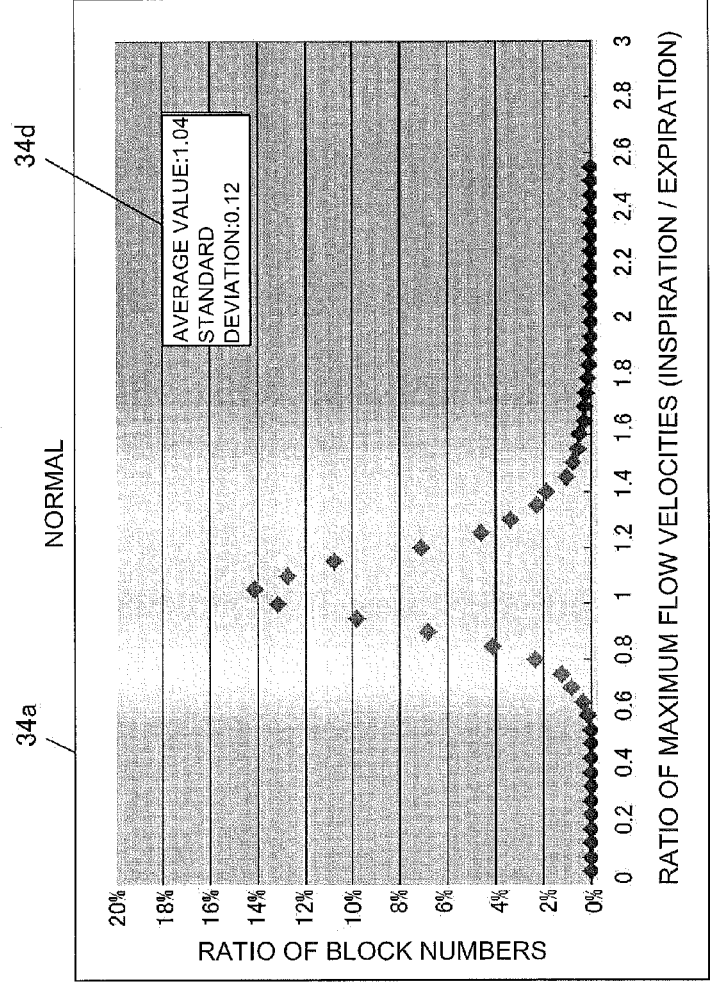
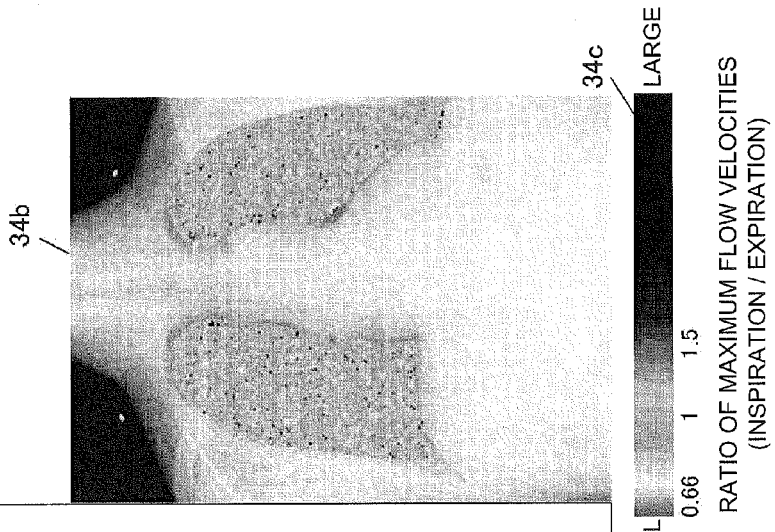

COEFFICIENT OF
VARIATION, SMALL

COEFFICIENT OF
VARIATION, LARGE

FIG. 17
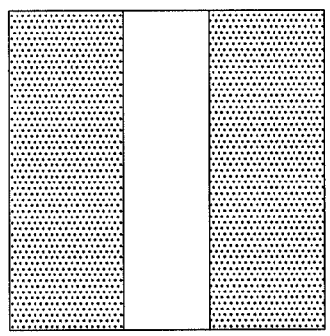
BEFORE BLOOD
VESSEL
EXPANSION
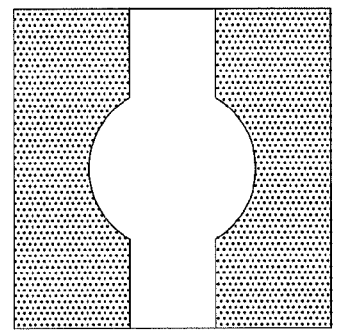
TIME OF BLOOD
VESSEL
EXPANSION FIG. 23
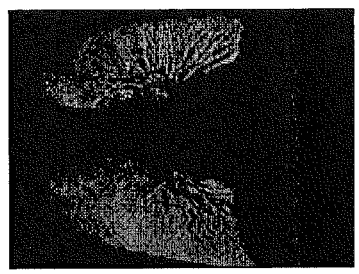

CHEST DIAGNOSTIC SUPPORT INFORMATION GENERATION SYSTEM

This application is based on Japanese Patent Application No. 2011-115601 filed on May 24, 2011, in Japan Patent Office, the entire content of which is hereby incorporated by reference.

TECHNICAL FIELD

The present invention relates to a chest diagnostic support information generation system.

BACKGROUND

Motion images of the diagnostic subject portion taken by using a semiconductor image sensor such as FPD (Flat Panel Detector) are increasingly tried to be applied to diagnosis, compared with conventional still imaging and diagnosis using films or photostimulable phosphor plates. Specifically, by utilizing the quick response in reading and erasing image data of semiconductor image sensors, continuous irradiation or consecutive pulsed irradiation is carried out from a radiation source corresponding to a timing of reading and erasing of the semiconductor image sensor to take plural images per second and thereby the motion image of the diagnostic portion is taken. A doctor can recognize the series of movements of the inspection portion (body parts) by sequentially displaying the each of the plural images obtained by the imaging.

Further it has been proposed to analyze series of frame images obtained by motion imaging to generate diagnostic support information and supply the doctor with it for quick diagnosis.

For example, in Japan Patent Application Publication No. 2009-136573, a technology that, by assuming that a blood density varies depending on a blood flow, detects a chunk part of blood expelled out from a heart based on the density variation in a blood vessel and detects a blood flow speed and so on by series of frame images obtained by motion imaging the chest portion is described.

Further, in International Application Publication 2009/090894, a technology that calculates frame difference values between adjacent frame images of series of frame images and judges whether or not the breathing (respiration) and the blood flow are abnormal based on the calculated frame differences is described.

BRIEF DESCRIPTION OF THE INVENTION

Problems to be Solved by the Invention

In Japan Patent Application Publication No. 2009-136573, position shifts of the blood vessel region have to be prevented in order to perform an accurate analysis, that is, it is necessary to stop the breathing, further the feature amount relating to the breathing can not be calculated. In International Application Publication 2009/090894, although both the feature amounts relating to the breathing and the blood flow can be calculated by the imaging data of one time, quite an amount of processing time is required in order to get an accurate analysis result because a warping processing at each accurate small region becomes indispensable, and there is a defect that it is difficult to obtain the relating to blood flow as accurate as the feature amount relating to the breathing because both the feature amount are calculated by the same processing algorism (difference signal value between frames).

By the way, as understood from that the cardiac beat rate is measured by counting the pulsation number by palpating a wrist artery, a partial expansion of blood vessel (pulsation) travels throughout the lung blood vessel when blood flows from the heart to the lung blood vessel. The expansion of lung blood vessel reflects on a signal value output of detecting elements of a radiation detection device corresponding to the expanded part and the amount of the signal value change (amount of signal change of the blood vessel region with respect to a non blood vessel region) is relatively large. Therefore, the inventors of the present invention have found that the diagnostic support information relating to blood flow can be extracted more accurately and supplied to the doctor, by analyzing the series of frame image data obtained by motion imaging the chest portion of the subject based on the signal value difference which is different from that of the feature amount processing of breathing.

SUMMARY OF THE INVENTION

One aspect of the present invention is to supply accurate diagnostic support information relating to each of the breathing and the blood flow by one time of motion imaging.

To solve at least one of the above mentioned problem, a chest diagnostic support information system reflecting one aspect of the present invention, comprises: a radiography section which radiographs a chest portion of a subject by using a radiation source and a radiation detector which generates an image data of the subject by detecting by a plurality of detection elements arranged two dimensionally, radiation having penetrated through the subject which is irradiated from the radiation source; an image analysis section which generates a diagnostic support information relating to the chest portion of the subject based on the image data generated by the radiography section; and a display which displays the diagnostic support information generated by the image analysis section, wherein the radiography section is configured to be capable of obtaining a plurality of frame images which show a motion state of the chest of the subject by irradiating radiation continuously from the radiation source, and the image analysis section comprises: a breathing information generation section which, for the plurality of frame images obtained by the radiography section, corresponds a pixel or a block pixel with each other which represents signal values which a detection element of a same position in the radiation detector among the plurality of image frames outputs, and generates the diagnostic support information relating to breathing of the subject based on a difference value of the pixel or the block pixel corresponded with each other between image frames temporally adjacent; and a blood flow information generation section which, for the plurality of frame images obtained by the radiography section, correspond a pixel or a block with each other which represents signal values which the detection element of the same position in the radiation detector among the plurality of image frames outputs, generates an output signal wave form which represents a temporal change of signal values of the pixel or the block corresponded with each other, and generates the diagnostic support information relating to blood flow of the subject based on the generated output signal wave form.

BRIEF DESCRIPTION OF THE DRAWINGS

FIG. 12A is a figure showing an example of the display screen which displays the analysis result obtained by analyzing the motion image of a lung field of a normal person;

FIG. 17 is a figure showing schematically an expansion of the lung blood vessel by the blood flow.

FIG. 23 is figures showing the example of a display of the diagnostic support information relating to blood flow;

PREFERRED EMBODIMENT OF THE INVENTION

Embodiments of the present invention will now be described with reference to the drawings. However, the scope of the invention is not limited to the illustrated examples.

1st Embodiment

Configuration of the Chest Diagnostic Support Information Generation System 100

The configuration of the 1st embodiment is explained first. The whole configuration of the chest diagnostic support information generation system 100 of the 1st embodiment is shown in FIG. 1.

Figure 1:
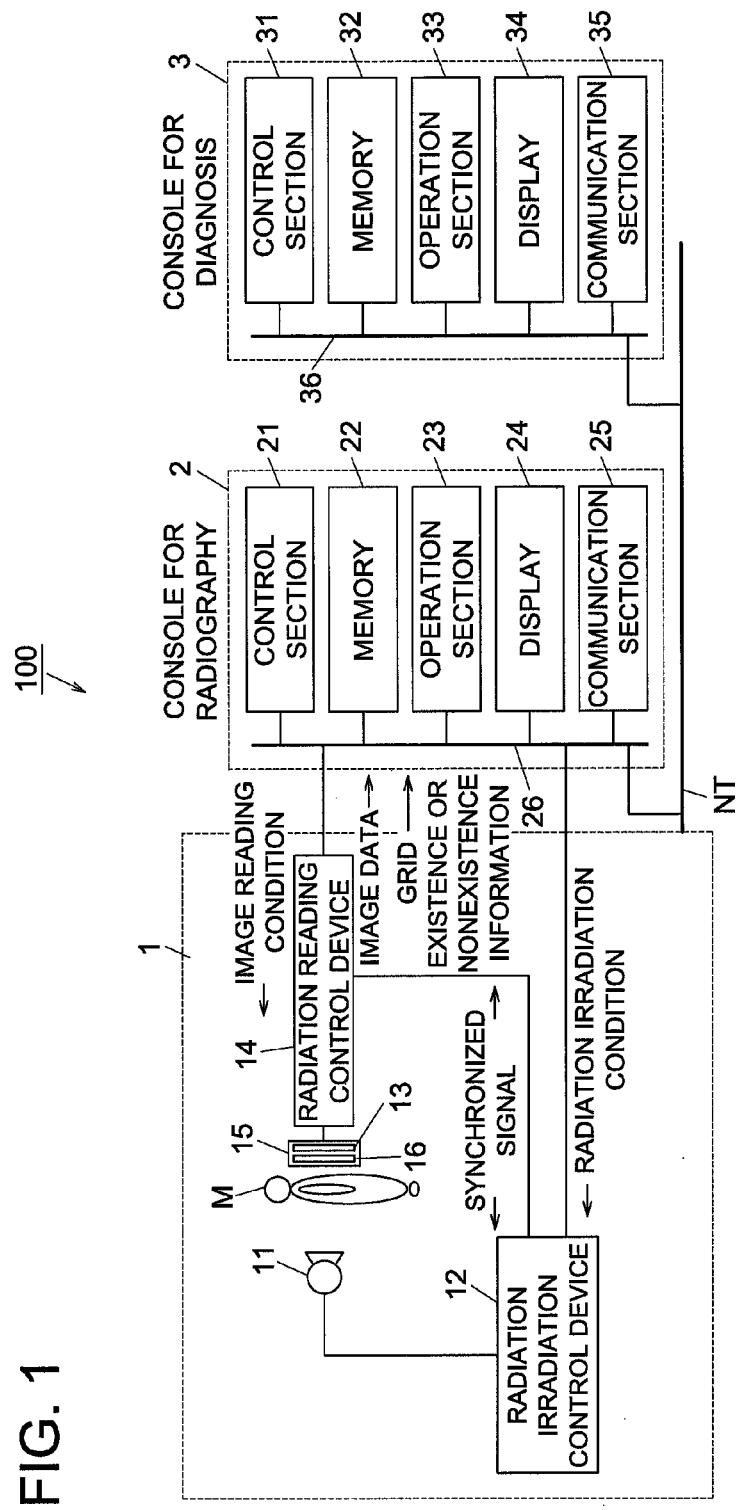
FIG. 1 is a figure showing the whole configuration of the chest diagnostic support information generation system of the 1st embodiment.

As shown in FIG. 1, the chest diagnostic support information generation system 100 is configured by that a radiography equipment 1 and a console for radiography 2 are connected via a telecommunication cable and so on, and the console for radiography 2 and a console for diagnosis 3 are connected via a communication network NT, such as LAN (Local Area Network). Each equipment which constitutes the chest diagnostic support information generation system 100 is in accordance with DICOM (Digital Image and Communications in Medicine) standard, and communication between each equipment is performed in conformity with DICOM.

Configuration of Radiography Equipment 1

Radiography equipment 1 is an equipment which irradiates radiation to a subject M (chest of a human body), and performs a motion imaging or a still imaging of the subject M.

The motion imaging means obtains plural images (namely, continuation radiography) by a continuous irradiation or plural pulsed irradiation of the radiation such as X-rays in pulsed mode to the subject M. In motion imaging, the motion state with a periodicity (cycle) of the radiographic subject M, such as a form change of expansion and contraction of the lung accompanying breathing movement and a pulsation of the heart is radiographed, for example. Series of images obtained by this continuation radiography are called as motion image, and each of the plural images which constitute the motion image is called as frame image.

The still imaging is used for diagnosis based on the density resolution of the radiographed portion similar to the conventional film system and the conventional CR system, and means obtaining a still image of one sheet by irradiating once radiation such as X-rays to the subject M.

The radiography equipment 1 is constituted by a radiation source 11, a radiation irradiation control device 12, a radiation detector 13, a reading control device 14, a holding portion 15, a grid 16, and so on, as shown in FIG. 1.

The radiation source 11 is a radiation generating equipment which can perform a single irradiation and a continuous irradiation (a type of plural pulsed irradiation). Another type (a type of continuous irradiation) could be available. In other word, the radiation source 11 is a radiation generating equipment applicable for both still imaging and motion imaging. The radiation source 11 is arranged on an opposite sides of the radiation detector 13 with respect to the radiographic subject M and irradiates radiation (X-rays) to the radiographic subject M according to the control of the radiation irradiation control device 12.

The radiation irradiation control device 12 is connected with the console for radiography 2, and irradiates radiation based on a radiation irradiation conditions input from the console for radiography 2 through controlling the radiation source 11. The radiation irradiation conditions input from the console for radiography 2 are a pulse rate at the time of continuation irradiation, a pulse width, a pulse interval, a number of radiography frames per one radiography, a value of X-ray tube current, a value of X-ray tube voltage, a filter type, and so on, for example. The pulse rate is the number of times of radiation irradiation per second, and corresponds with a frame rate mentioned later. The pulse width is a radiation irradiation time per one radiation irradiation. The pulse interval is, in continuation radiography, a time from one radiation irradiation start to the next radiation irradiation start, and corresponds with the frame interval mentioned later.

Figure 2:
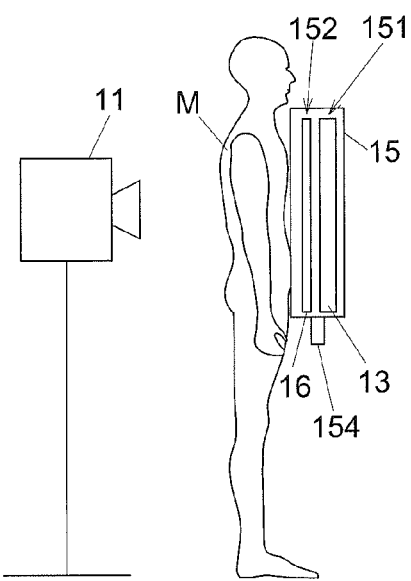
FIG. 2 is a figure expanding and showing the holding portion 15 and the vicinity of the holding portion 15 of FIG. 1.

The radiation detector 13 is configured by FPD and so on compatible with motion imaging and still imaging. The FPD, for example, is provided with a glass substrate and so on, and plural pixels arranged in a matrix shape which detects the radiation penetrated at least through the radiographic subject M irradiated from the radiation source 11 at a predetermined position on the substrate corresponding to the intensity, and changes the radiation into an electric signal and accumulates it. Each pixel is constituted by a switching part, such as TFT (Thin Film Transistor), for example. FPD of an indirect conversion type which changes X-rays into an electric signal by a photoelectric conversion element through scintillator or a direct conversion type which changes X-rays into an electric signal directly can be used. As shown in FIG. 2, the radiation detector 13 is held by the holding portion 15 such that the radiation detector 13 is disposed on the opposite side of the radiation source 11 in respect to the radiographic subject M.

The reading control device 14 is connected with the console for radiography 2.

The reading control device 14 controls the switching part of each pixel of the radiation detector 13 to obtain image data (a still image or a frame image) by switching the reading of the electric signal accumulated in each pixel and reading the electric signal accumulated in the radiation detector 13, based on the image reading condition having been input from the console for radiography 2. And the reading control device 14 outputs the obtained image data to the console for radiography 2. The image reading condition is, for example, a frame rate, a frame interval, pixel size (binning size), image size (matrix size), and so on. The frame rate is the number of frame images obtained per second, and corresponds with the pulse rate. The frame interval is the time from one obtaining operation start of a frame image to the obtaining operation start of the following frame image in continuation radiography, and conforms with the pulse interval.

Here, the radiation irradiation control device 12 and the reading control device 14 are connected with each other, exchange a synchronized signal with each other, and synchronize the radiation irradiation operation with the reading operation of each image. Further, in a dark reading time for obtaining at least one dark image for calculating the offset correction coefficient to be used for an offset compensation mentioned later, a set of reset-accumulation-data detecting-reset is performed without synchronizing with radiation irradiation operation in the state where radiation is not irradiated, however the dark reading may be performed before or after the series of motion imaging.

Further, in this embodiment, the analysis is performed in each motion state analysis without performing compensation processing such as the offset compensation processing, the gain compensation processing, and the defective pixel compensation processing. This is for giving priority to analysis speed. In case of pursuing the accuracy rather than the analysis speed, the offset compensation processing, the gain compensation processing, the defective pixel compensation processing, and so on may be performed.

Figure 3:
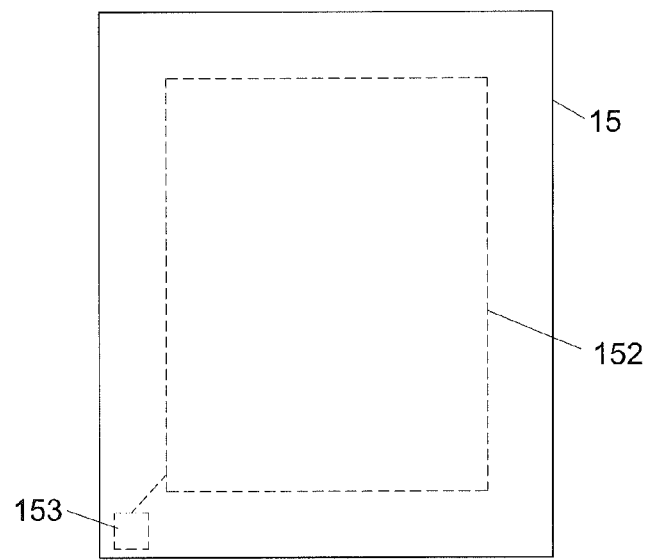
FIG. 3 is a figure showing schematically the front of the holding portion 15 of FIG. 1.

As shown in FIG. 2, the holding portion 15 has a detector holding portion 151 and holds the radiation detector 13 such that the radiation source 11 and the radiographic subject M face with each other at the time of radiography. Further, the holding portion 15 has a grid fixing part 152 for equipping with a grid 16 for removing dispersion radiation from the radiation detector 13 at the radiographic subject side (radiation source 11 side). That is, the holding portion 15 is configured such that the gird 16 is attachable and detachable. As shown in FIG. 3, a grid holding detection MS (micro switch) 153 for detecting whether the grid 16 is held at the grid fixing part 152, and the holding portion 15 outputs the detection signal of grid holding detection MS153 to the reading control device 14.

Further, as shown in FIG. 2, the holding portion 15 is provided with a radiographic subject detection sensor 154 for detecting whether the radiographic subject M exists within a predetermined area or not, and outputs the detection signal of the radiographic subject detection sensor 154 to the console for radiography 2 through the reading control device 14.

Configuration of the Console for Radiography 2

The console for radiography 2 controls the operations of the radiography and the reading of the radiation image through outputting radiation irradiation condition and image reading condition to the radiography equipment 1, generates suitably an image based on the still image or the motion image obtained by the radiography equipment 1, for example, such as a preview image subject to a thinning and binning processing and a processed image subject to a tone processing, and displays the image for checking whether or not a positioning by a radiographer is suitable and the image is suitable for diagnosis. It is also possible to use the difference image between the adjacent frames for checking the positioning or the motion cycle (cycle) of the part for the analysis object as the preview display in the case of the motion image. As shown in FIG. 1, the console for radiography 2 is configured by that a control section 21, a memory 22, an operation section 23, a display 24, and a communication section 25 are provided, and each part is connected by bus 26.

The control section 21 is configured by a CPU (Central Processing Unit), a RAM (Random Access memory), and so on. The CPU of the control section 21 reads out a system program and the various processing programs memorized in the memory 22 according to operation of the operation section 23, and develops them in the RAM. The CPU of the control section 21 performs various processings including the radiography control processing mentioned later according to the developed program, and performs an integration control of the operation of each part of the console for radiography 2, and radiation irradiation operation and detecting operation of radiography equipment 1.

The memory 22 is configured by a nonvolatile semiconductor memory, a hard disk, and so on.

The memory 22 memorizes the various programs executed in the control section 21, parameters required for executing processing according to the program, and data such as processing results. For example, the memory 22 has memorized the radiography control processing program for performing radiography control processing shown in FIG. 4. Various programs are stored in forms of the readable program code, and the control section 21 performs operations according to the program code sequentially.

Further, the memory 22 has memorized radiation irradiation condition and image reading condition for each of motion imaging and still imaging.

The operation section 23 is provided with a keyboard equipped with cursor keys, number input keys, various function keys and so on, and a pointing devices such as a mouse, and outputs the directions signal input by the key operation to the keyboard, or the mouse operation to the control section 21. Further, the operation section 23 may have the display screen of the display 24 with a touch panel, and outputs the direction signal input, in this case, through the touch panel to the control section 21.

The display 24 is configured by a monitors such as LCD (Liquid Crystal Display) and CRT (Cathode Ray Tube), and displays input directions from the operation section 23, data, and so on according to the directions of the display signal input from the control section 21.

The communication section 25 has a LAN adapter, a modem, TA (Terminal Adapter) and so on, and controls the data transmission and reception between each equipment connected to the communication network NT.

Configuration of the Console for Diagnosis 3

The console for diagnosis 3 is a computer device to obtain a still image or motion image (series of frame images) from the console for radiography 2, display diagnostic support information including the obtained image, the histogram mentioned later, and so on, for the diagnostic radiograph interpretation by the doctor.

As shown in FIG. 1, the console for diagnosis 3 is configure by that a control section 31, a memory 32, an operation section 33, a display 34, and a communication section 35, which are connected with each others by bus 36 are provided.

The control section 31 is configured by a CPU, a RAM, and so on. The CPU of the control section 31 reads out system program and various processing programs memorized in the memory 32, according to operation of the operation section 33, develops in the RAM, performs various processings including the image analysis processing mentioned later, and performs an integrated control of the operation of each part of console for diagnosis 3 according to the developed program.

The memory 32 is configured by nonvolatile semiconductor memory, a hard disk, and so on.

In the memory 32, various programs including the image analysis processing program for performing image analysis processing in the control section 31, parameters required for the execution of processing by the programs and the data of processing results and so on are memorized. These various programs are stored in the forms of readable program codes and the control section 31 performs operation according to the program codes sequentially.

The operation section 33 is configured by that a keyboard equipped with a cursor key, a number input key, various function keys, a pointing device such as a mouse and so on are provided, and outputs the direction signal input by the key operation to the keyboard, or mouse operation to the control section 31. Further, the operation section 33 may have the display screen of a display 34 with a touch panel, and, in this case, outputs the direction signal input through the touch panel to the control section 31.

The display 34 is configured by a monitor, such as LCD and CRT, and displays the input direction from the operation section 33, data, and so on according to the direction of the display signal input from the control section 31.

The communication section 35 is provided with a LAN adapter, a modem, TA, and so on, and controls data transmission and reception among each of the equipments connected to the communication network NT.

Operation of the Chest Diagnostic Support Information Generation System 100

Next, operations in the chest diagnostic support information generation system 100 are explained.
(Operation of the Radiography Equipment 1 and the Console for Radiography 2)

A radiography operation by radiography equipment 1 and the console for radiography 2 are explained first.

Figure 4:
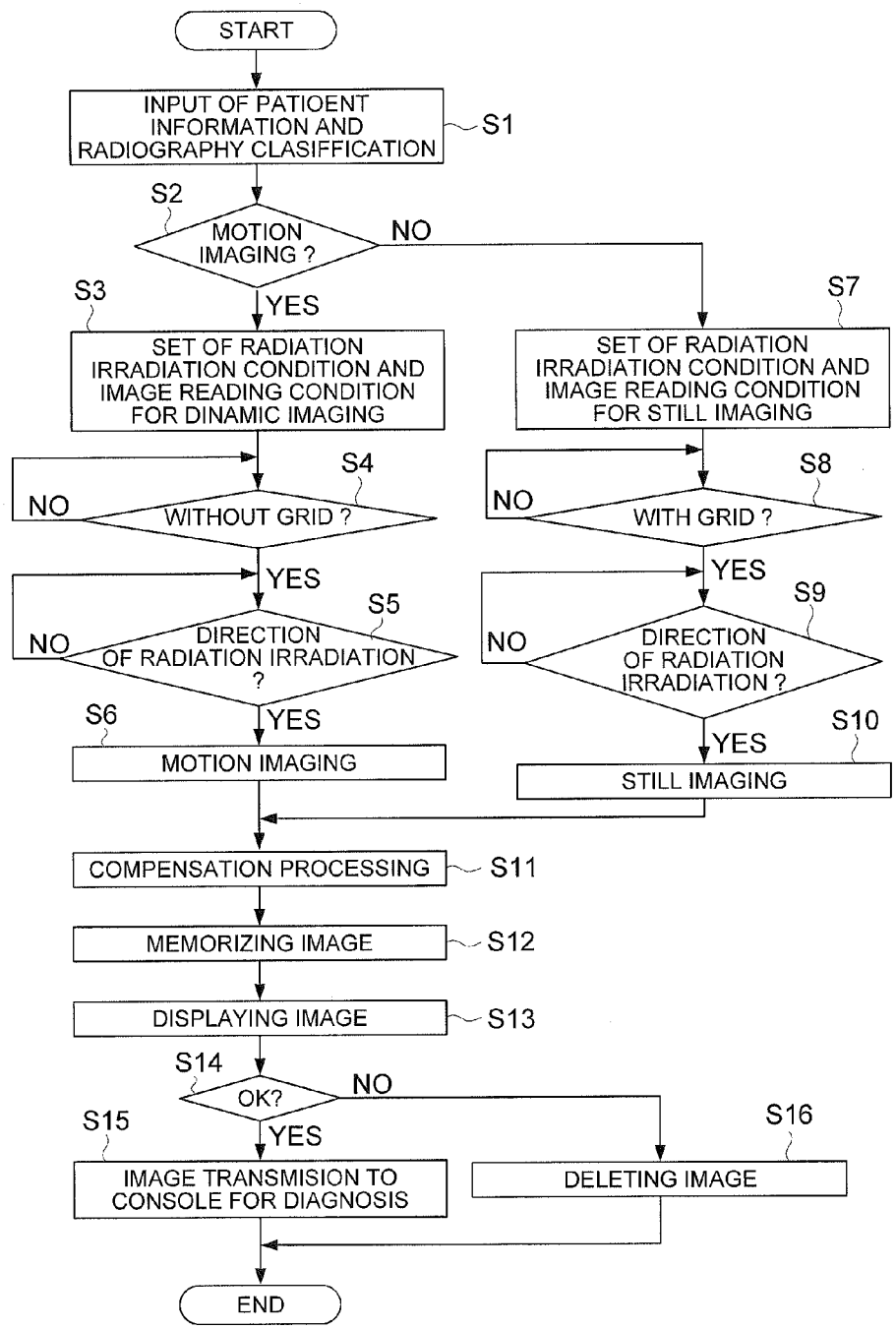
FIG. 4 is a flow chart which shows the radiography control processing performed by the control section of the console for radiography of FIG. 1.

The radiography control processing performed in the control section 21 of the console for radiography 2 is shown in FIG. 4. The radiography control processing is performed by the control section 21 by collaborating with the radiography control processing program memorized in the memory 22.

First, the operation section 23 of the console for radiography 2 is operated to input the patient information including patient's name, height, weight, age, sex, and so on for the radiographic subject (radiographic subject M) and a radiography classification (motion imaging or still imaging) by the radiographer, (Step S1). In addition, similarly, received data which has been transmitted from another equipment which is not illustrated, connected to the communication network NT via the communication section 25, also can be regarded as input information.

Subsequently, it is judged whether the input radiography classification is motion imaging or still imaging (Step S2). If it is judged that the input radiography classification is motion imaging (Step S2; YES), while an image detecting condition for motion imaging is read from the memory 22 and is set to the reading control device 14, the radiation irradiation condition for motion imaging is read from the memory 22 and is set to the radiation irradiation control device 12 (Step S3). If it is judged that the input radiography classification is still imaging (Step S2; NO), while an image detecting condition for still imaging is read from the memory 22 and is set to the reading control device 14, the radiation irradiation conditions for still imaging is read from the memory 22 and is set to the radiation irradiation control device 12 (Step S7).

The preferable frame rate for the present embodiment which analyzes both the feature amount relating to breathing and the feature amount relating to blood flow is 7.5 or more frame rate per second and more preferably 15 or more frame per second. In addition, when analyzing only the feature amount relating to breathing, 3.5 or more frame per second is preferable and 7 or more frame rate per second is more preferable.

Further, in the embodiment, the radiation irradiation condition based on imaging in a state where a grid 16 is not installed (without grid) is set up for motion imaging and the radiation irradiation condition based on imaging in a state where the grid 16 is installed (with a grid) is set up for still imaging. Specifically, the radiation irradiation condition in which the sum of the radiation dose which reaches the radiation detector 13 without using the grid 16 for each one frame image in the radiography of motion imaging becomes the same as the radiation dose which reaches the radiation detector 13 in still imaging using the grid 16 is setup. That is, in motion imaging, the radiation irradiation condition is set up so that the radiation dose per each frame becomes lower, compared with still imaging.

Here, when irradiating radiation to the radiographic subject M such as a human body to performing radiography, the radiation which penetrates the inside of the body is scattered by the body tissue. And if such scattered radiation enters into the radiation detector 13, a noise will occur in the radiation image. Therefore, it is preferable to radiograph with arranging the grid 16 at a face of a radiographic subject side of the radiation detector 13 which is the side into which the radiation having penetrated the radiographic subject enters, for a still image of which an absolute output signal (representing density and contrast) of each pixel is important and is used for a detection of a pathological change portion, an observation of a pathological change portion, and so on, When radiographing with grid, since the radiation dose which reaches the radiation detector 13 decreases by the grid 16 (For example, it is reduced to one half when a grid with a bucky factor of 2 is used), it is necessary to irradiate the radiation by the amount equivalent to the amount reduced. Conventionally, also in motion imaging, imaging has been performed with grid, as same as in still imaging.

However, since the number of the frame images used in motion imaging is larger compared with still imaging, when the radiation dose to be irradiated in each frame from the radiation source 11 is made equivalent to still imaging, there is a problem that the radiation dose of the radiographic subject M will increase in motion imaging. Although the technology which makes the same the radiation dose of one still imaging and the total radiation dose of the series of motion imaging to be equivalent, in order to reduce the amount of the radiation dose of the radiographic subject M is also disclosed, the radiation dose of each frame image will tend to be insufficient in this case, and the S/N ratio will decrease.

Therefore, the inventor's of the present invention, through repeating examinations wholeheartedly, have found out that the chest motion image obtained by motion imaging is used mainly for motion state analyses for a breathing function, a blood flow and so on, and, in these analyses, an equivalent result even in the case when the motion image is taken without arranging a grid to the case when the motion image is taken with using the grid can be obtained. In other words, if the radiation dose which reaches the radiation detector is the same, regardless of existence or nonexistence of the grid, an almost equivalent analysis result can be obtained (refer to FIG. 11. Details are explained later.)

In the chest diagnostic support information generation system 100 of the embodiment based on this knowledge, in still imaging, the radiograph is taken with equipping with the grid 16 (with grid), and in motion imaging (in conducting motion state analysis), the radiograph is taken without equipping with the grid 16 (without grid). The chest diagnostic support information generation system 100 is configured to reduce the radiation dose of the radiographic subject M while the radiation dose reaching to the radiation detector 13 is maintained almost equal as before, by performing radiography on the radiation irradiation condition in which the radiation dose which reaches the radiation detector 13 at the time of the still imaging using the grid 16 is almost equivalent to the radiation dose which reaches the radiation detector 13 of the radiography during the motion imaging without using the grid 16. Further, the S/N ratio of each frame image may be raised up compared with the conventional motion imaging system to aim to improve the analysis accuracy by performing radiography with grid in still imaging and performing radiography without grid in motion imaging while the radiation irradiation condition in which the total radiation dose of one still imaging is equivalent to the series of motion imaging is kept.

When the radiation irradiation condition and image detecting condition for motion imaging are set, it is judged whether or not it is in the state where the grid fixing part 152 is equipped with the grid 16 based on the output from grid holding detection MS153 (Step S4).

If it is judged that it is in the state where the grid fixing part 152 is not equipped with the grid 16 (Step S4; YES), the direction of the radiation irradiation by the operation at the operation section 23 will stand by (Step S5). Here, in order to radiograph the motion state of quiet breathing, a radiographer instructs the examined person (radiographic subject M) to be relieved to make a quiet breathing. When the radiography preparation is ready, the operation section 23 is operated to input the radiation irradiation direction.

If the radiation irradiation direction is input by the operation section 23 (Step S5; YES), the directions to start radiography is output to the radiation irradiation control device 12 and the reading control device 14, and motion imaging will be started (Step S6). That is, radiation from the radiation source 11 is irradiated with the pulse interval set by the radiation irradiation control device 12, and a frame image is obtained by the radiation detector 13. After the radiography of the predetermined number of frames is completed, the direction of the end of radiography is output to the radiation irradiation control device 12 and the reading control device 14 by the control section 21, and the radiography operation is stopped. The number of frames to be radiographed is the number corresponding to at least one quiet breathing cycle.

On the other hand, when the radiation irradiation condition and image detecting condition for still imaging are set, whether or not it is in the state where the grid fixing part 152 is equipped with the grid 16 is judged based on the outputs from grid holding detection MS153 and the radiographic subject detection sensor 154 (Step S8). The control section 21 controls, according to the step S8, so that still imaging is not performed without being equipped with a grid 16.

If it is judged that the grid fixing part 152 is equipped with the grid 16 (Step S8; YES), the direction of the radiation irradiation by the operation at the operation section 23 will stand by (Step S9). Here, the radiographer directs the examined person to stop breathing after breathing air in when the radiography preparation is ready, and the radiation irradiation direction is input through the operation at the operation section 23.

When the radiation irradiation direction is input at the operation section 23 (Step S9; YES), the radiography start direction will be output to the radiation irradiation control device 12 and the reading control device 14, and still imaging will be performed (Step S10).

After the motion imaging or the still imaging is completed, the image (each frame image or a still image) obtained by radiography is input into the console for radiography 2 sequentially, and the compensation processing is performed (Step S11). In the compensation processing of Step S11, three compensation processings of offset compensation processing, gain compensation processing, and defective pixel compensation processing are performed according to need. In the embodiment, the control section 21 controls to perform these compensations in still imaging, and not to perform these compensations when an image analysis processing later mentioned is performed in motion imaging.

Here, a delicate change of the density value of the structure of the portion for diagnosis in the diagnostic imaging using a still image is observed. Therefore, the offset compensation processing, the gain compensation processing, and so on for suppressing, as much as possible, the output variation of each detection element of FPD, are indispensable. The offset compensation processing is a processing which removes the offset value, resulted from the dark current, which overlaps on each frame image. The gain compensation processing is a processing which removes a variation for each pixel produced by the individual specificity of each detection element corresponding to each pixel of each frame image, or a gain unevenness of the read-out amplifier.

However, when computing the feature amount relating to the motion, plural frame images are needed. For example, when computing the feature amount of ventilation of lungs, average breathing cycle of adult is around 3.3 seconds, and since the image of at least one cycle is needed for calculating the feature amount, the radiography time is needed to be set about 4 seconds. In this case, if the frame rate is five frames per second, the image data of 20 frames is needed. Since the time for about 0.5-1 second will be required per one-frame image if the offset processing and gain compensation processing are performed to each frame, it will take about 10 to 20 seconds to perform the processings to the 20 frames.

Further, when a more faithful offset compensation processing is performed, at least one dark reading (FPD reading at the time of non-radiation irradiating) will be performed after the radiography of each frame image. At this case, in the FPD, since the image obtaining at the frame rate at least more than two times of the intended frame rate is needed, it is not preferable as the hardware configuration increases in complexity accompanied by the increase of the speed and the power consumption will also increase.

Further, in order to transmit the frame image and dark image which are output from FPD to the console to perform offset compensation processing, the transmitting time of the dark image is also needed in addition to the transmission of each frame image. Further, although dark reading of one time or a number of times less than the number of the frame image when the radiation is irradiated and carrying out offset compensation processing to all the frame images using these dark images may be also considered, the time to carry out offset compensation processing using the obtained dark image is required, though the frame rate which is needed for dark image reading is reduced compared with the case where dark image reading is performed next to each frame image. Further, the calculation processing of the feature amount relating to motion state also has the defect that the calculation processing of the feature amount cannot be started unless after carrying out the offset compensation processing.

Then, in the embodiment, in performing the image analysis processing later mentioned by motion imaging, the offset compensation processing, the gain compensation processing, and the defective pixel compensation processing are not performed.

In this embodiment, feature amount is calculated based on the difference between neighboring frames per each pixel or each small area which includes predetermined number of pixels. So, the difference is not influenced or less influenced by output change of each pixel due to the offset, gain and defective above mentioned and the calculation processing time is reduced.

In addition, for the offset correction coefficient, the gain correction coefficient, and the defective pixel position information map which are used in the offset compensation processing, the gain compensation processing, and the defective pixel compensation processing, optimal values respectively according to collection modes such as binning and a motion range are beforehand memorized and the optimal value corresponding to each collection mode is read out. Further, it is preferable to perform thinning processing, gradation processing, and so on with respect to the image obtained if needed.

Subsequently, while the image after compensation processing is memorized in the memory 22 (Step S12), the image after compensation processing is displayed on the display 24 (Step S13). When the motion imaging is performed, each frame image is corresponded with the number which shows the order of radiography and is memorized in the memory 22. Here, the obtained image may be memorized after performing logarithmic transformation processing which converts the signal value of each pixel from a true number into logarithm number just before memorizing the obtained image. The radiographer checks positioning and so on by the displayed motion image, and judges whether the image obtained by radiographing is suitable for diagnosis (radiography OK) or re-radiography is necessary (radiography NG). And the operation section 23 is operated to input the judgment result. In addition, each frame image obtained by the radiography may be summarized to be input at once after the completion of all the radiography. In addition, each frame image without compensation (raw data of each frame image outputted by the detector) can be displayed in every time when the console received each frame image before memorizing. In this case, the radiographer can judge the positioning quickly.

If the judgment result which shows radiography OK by the predetermined operation of the operation section 23 is input (Step S14; YES), Information such as Identification ID for identifying a image, patient information and a portion to be examined, radiation irradiation condition, image reading condition, frame number which shows the order of radiography, day and time of the radiography, and information which shows the existence or nonexistence of the grid at radiography (grid existence or nonexistence information) is attached (for example, is written in the header area of image data in DICOM form) to the still imaging obtained by still imaging and each of the series of frame images obtained by the motion image and are transmitted to the console for diagnosis 3 through the communication section 25 (Step S15). And this processing is ended. On the other hand, if the judgment result which shows radiography NG is input by the predetermined operation of the operation section 23 (Step S14; NO), the series of frame images memorized in the memory 22 is deleted (Step S16), and this processing is ended. In this case, re-radiography will be performed.

The lapsed time from a radiography start when certain frame image was taken can be obtained by the frame number and image reading condition (frame interval).

(Operation of the Console for Diagnosis 3)

Next, operation in the console for diagnosis 3 is explained. In the console for diagnosis 3, if the still image is received from the console for radiography 2 through the communication section 35 and display directions of the image are input at the operation section 33, the still image received is displayed at the display 34 and supplied for the diagnosis by the doctor. On the other hand, if the series of frame images of the motion image are received from the console for radiography 2 through the communication section 35 and motion state analysis is directed by the operation section 33, the image analysis processing shown in FIG. 5 is performed by the control section 31 in accordance with the image analysis processing program memorized in the memory 32.

Figure 5:
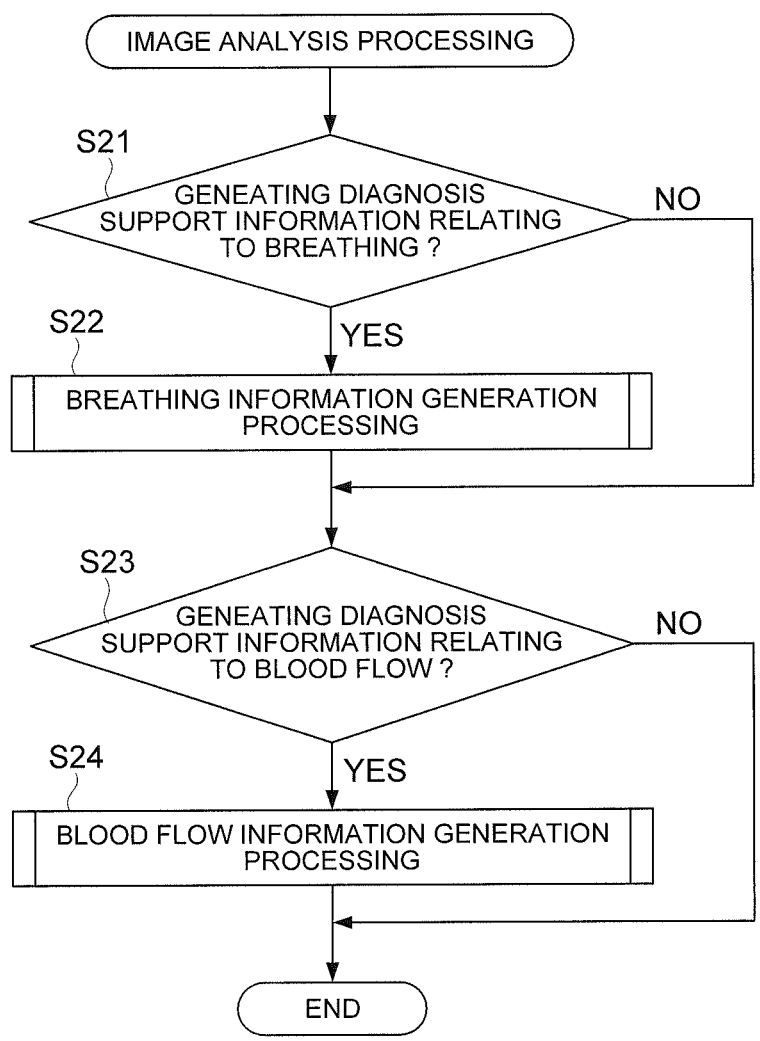
FIG. 5 is a flow chart which shows the image analysis processing performed by the control section of the console for diagnosis of FIG. 1.

The flow of image analysis processing with reference to FIG. 5 is explained hereafter.

First, the selection screen for choosing the kind of diagnostic support information (breathing, blood flow, breathing and blood flow) generated by the image analysis is displayed at the display 34 and, when it is judged that generation of the diagnostic support information relating to breathing has been selected from the selection screen by the operation section 33 (Step S21; YES), the breathing information generation processing will be performed (Step S22). When it is judged that generation of the diagnostic support information relating to blood flow has been selected (Step S23;YES), the blood-flow information generation processing will be performed (Step S24).

Figure 6:
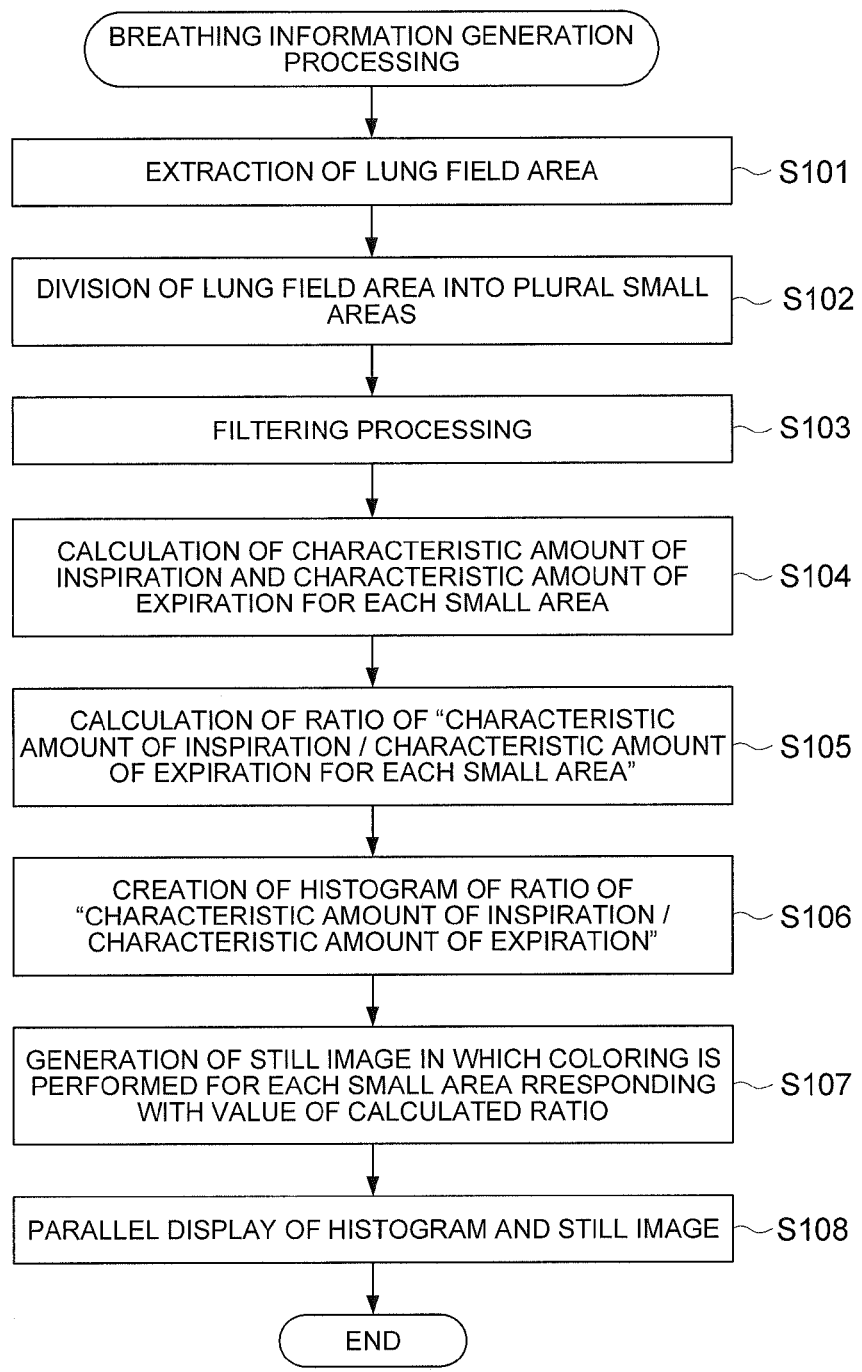
FIG. 6 is a flow chart which shows the breathing information generation processing performed by the control section of the console for diagnosis of FIG. 1.

Here, the breathing information generation processing performed in Step S22 of FIG. 5 is explained. The flow chart of the breathing information generation processing is shown in FIG. 6.

In the breathing information generation processing, the lung field area is first extracted from each frame image (Step S101).

The extraction method of the lung field area may be any method. For example, the threshold value is calculated by discriminant analysis from a histogram of the signal value (density value) of each pixel of the arbitrary frame image in the series of frame images (here, the first (beginning) frame image in the order of radiography is represented), and the area of higher signals than the threshold value is extracted in the primarily sampling as a lung field area candidate, Subsequently, if an edge is detected near the boundary of the lung field area candidate extracted in the primarily sampling and points where edges are maximum in the small areas near the boundary are extracted along the boundary, the boundary of the lung field area can be extracted.

Subsequently, the lung field area of the arbitrary frame image is divided into small areas which are composed of predetermined number of pixels, and the extracted lung area is applied to other frame images and the lung area in each other frame image is divided into same small area as that of the arbitrary frame image and the small area of each frame image is corresponded to each other (Step S102). The position of the each small area in the detector, namely the position of the predetermined number of pixels in the detector belonging to each small area, is memorized in RAM of the control section 31.

Figure 7:
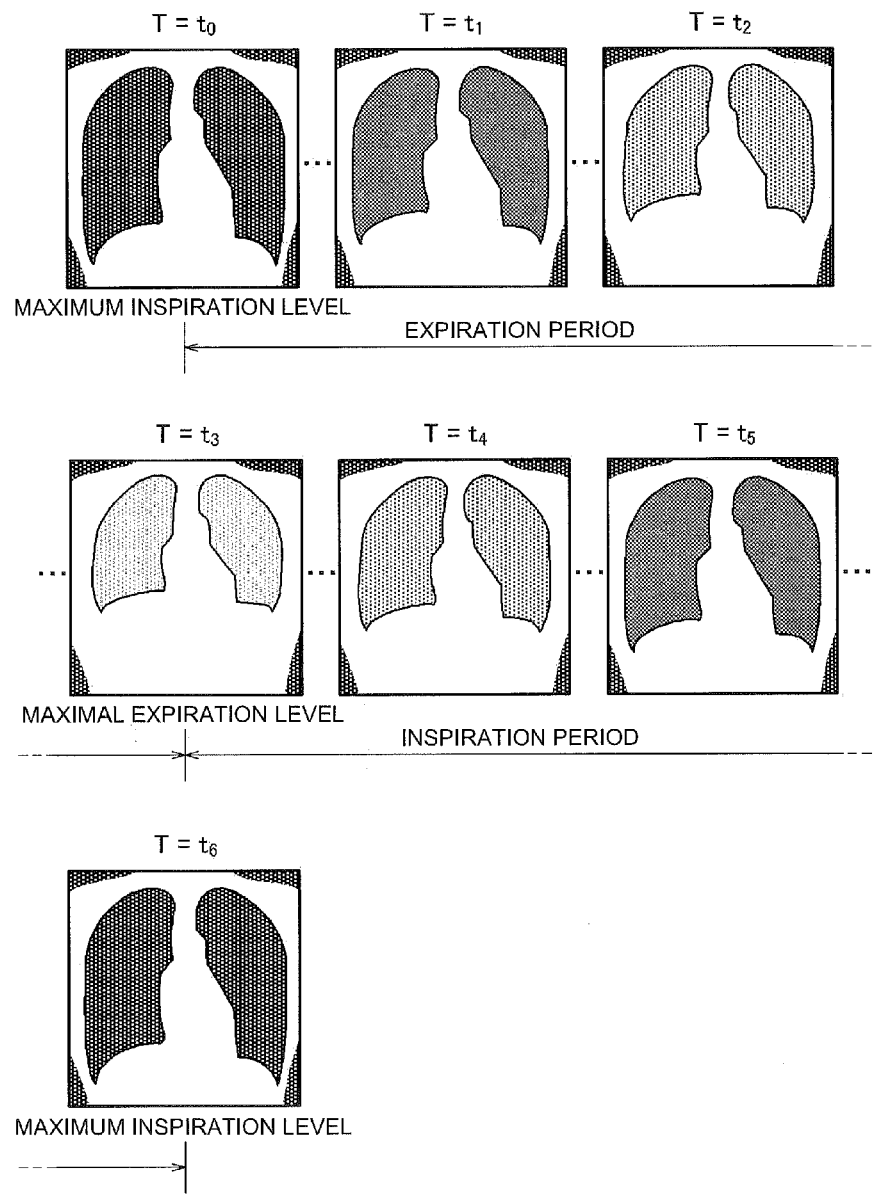
FIG. 7 is a figure showing plural time phases T (T=t0-t6) radiographed in one breathing cycle (at the time of deep breathing)

Here, a breathing cycle is constituted by an expiration period and the inspiration period. FIG. 7 is figures showing frame images of plural time phases T (T=t0-t6) radiographed in one breathing cycle (at the time of a deep breath). The expiration period, as shown in FIG. 7, air is discharged from the lung by an elevation of diaphragm and the area of the lung field becomes small. At the maximum expiration level, the position of a diaphragm will be in the highest state. At the inspiration period, air is taken into the lung by a descending of the diaphragm, and as shown in FIG. 7, the area of the lung field in a thorax becomes large. At the maximum inspiration level, the position of the diaphragm will be in the lowest state. That is, since the position of the same portion of the lung field area changes with time according to the breathing motion, the pixel position which shows the same portion (especially lower area (near the diaphragm)) of the lung field between each frame image will shift.

Figure 8:
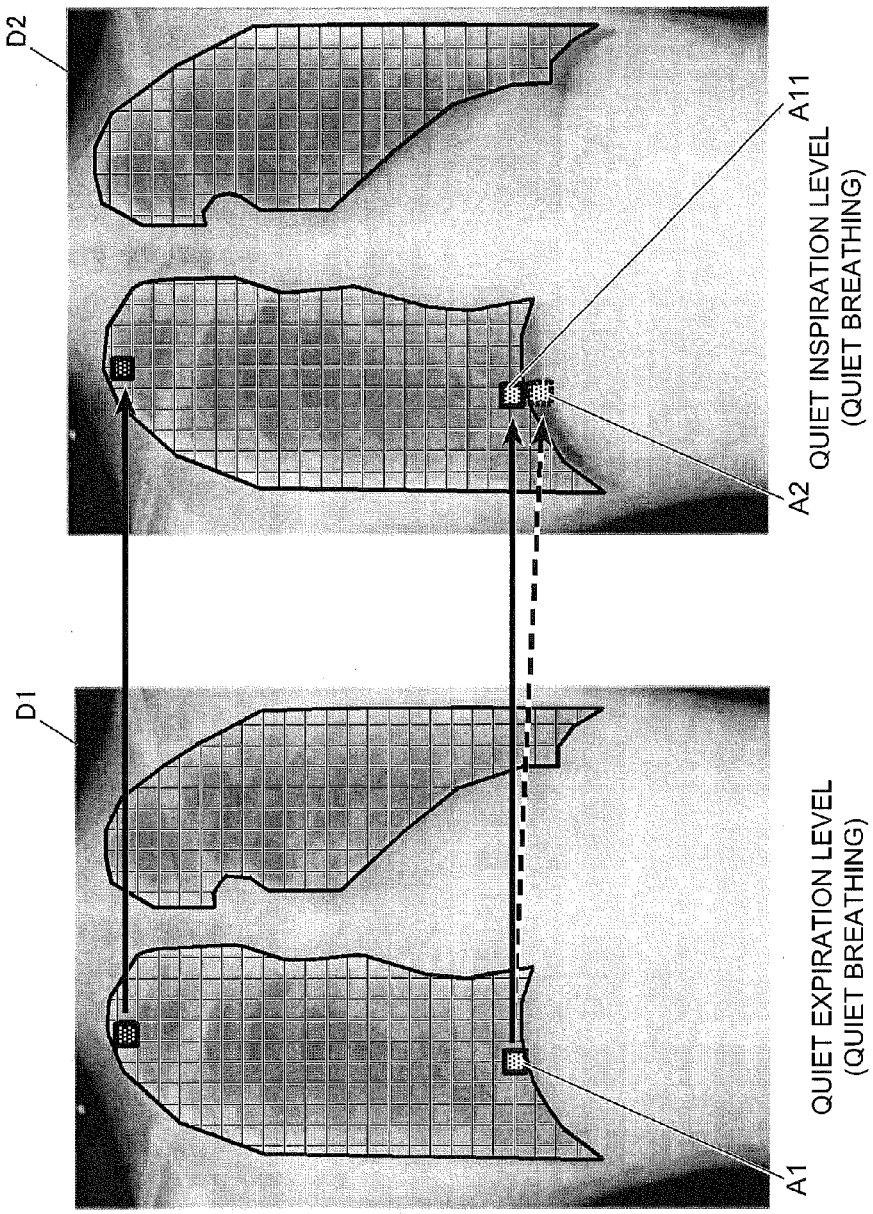
FIG. 8 is a figure showing changes of the positions of the area drawing the same portion of the lung field of a rest inspiration level and a rest expiration level.

However, in the image radiographed at the time of quiet breathing, the above-mentioned position gap is small and especially a position gap between neighboring frames is so small that the analysis result based on the difference between neighboring frames (mentioned later) is out of order will not happen. The image D1 of FIG. 8 is a frame image of the quiet expiration level (the timing as for which the position of the diaphragm has become the highest at the time of quiet breathing). The image D2 of FIG. 8 is a frame image of the quiet inspiration level (of the timing when the position of the diaphragm has become the lowest at the time of quiet breathing).

That is, the images D1 and D2 of FIG. 8 are images taken at the timings when the difference in form is the largest in one cycle breathing.

However, between the images D1 and D2 of FIG. 8, even in the lower area of the lung field area where a position gap is the largest, the position gap comes out to be not so large (All of the image D2 shows the same pixel position as A1 of the image D1, and A2 of the image D2 shows the area which draws the same portion in the lung field of A1 of the image D1).

First, as a standard image, one frame image (above mentioned arbitrary frame image) is set up out of the series of frame images, as a concrete processing in Step S102. Subsequently, the lung field area which has been extracted from standard image is divided into plural small areas (for example, square area of (2 mm×2 mm)) (refer to FIG. 8). Subsequently, other frame images are divided into the small area of the same pixel position as each small area of the standard image (area which shows the signal value output from the same pixel of the radiation detector 13). Subsequently, each small area of the same pixel position between each frame image is corresponded with each other. In other words, pixels in the FPD detector are divided into plural blocks, each of which corresponds to the each small area above mentioned, and each difference between neighboring frames over the motion image is calculated based on an output of pixels in each block. In this processing, it becomes possible to perform the division into small areas and the corresponding of the small areas of the frame image with a high speed.

As the standard image, the frame image in the maximum quiet expiration state is preferable. In the maximum quiet expiration state, the position of the diaphragm becomes the highest at the time of the quiet breathing, namely, since the area of the lung field area becomes the minimum, when the small area of the standard image is corresponded with other frame images, the small area is not corresponded with an area out side of the lung field of other frame images.

Figure 9:
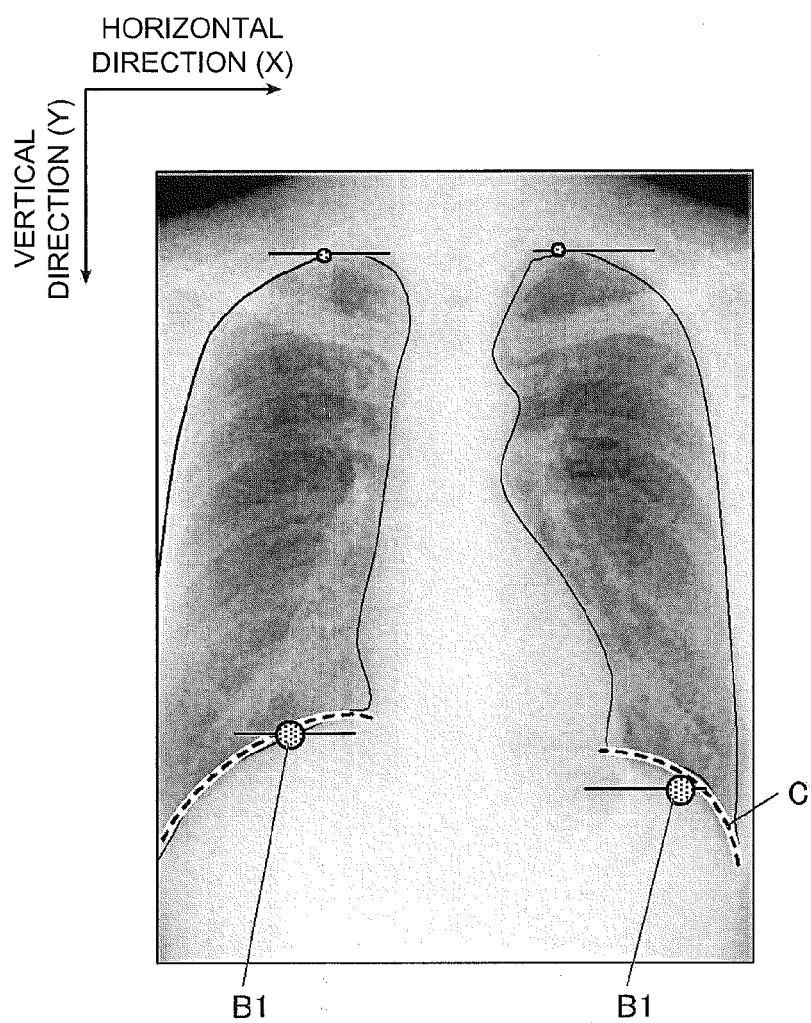
FIG. 9 is a figure for explaining the calculation method of the position of a diaphragm.
Figure 10:
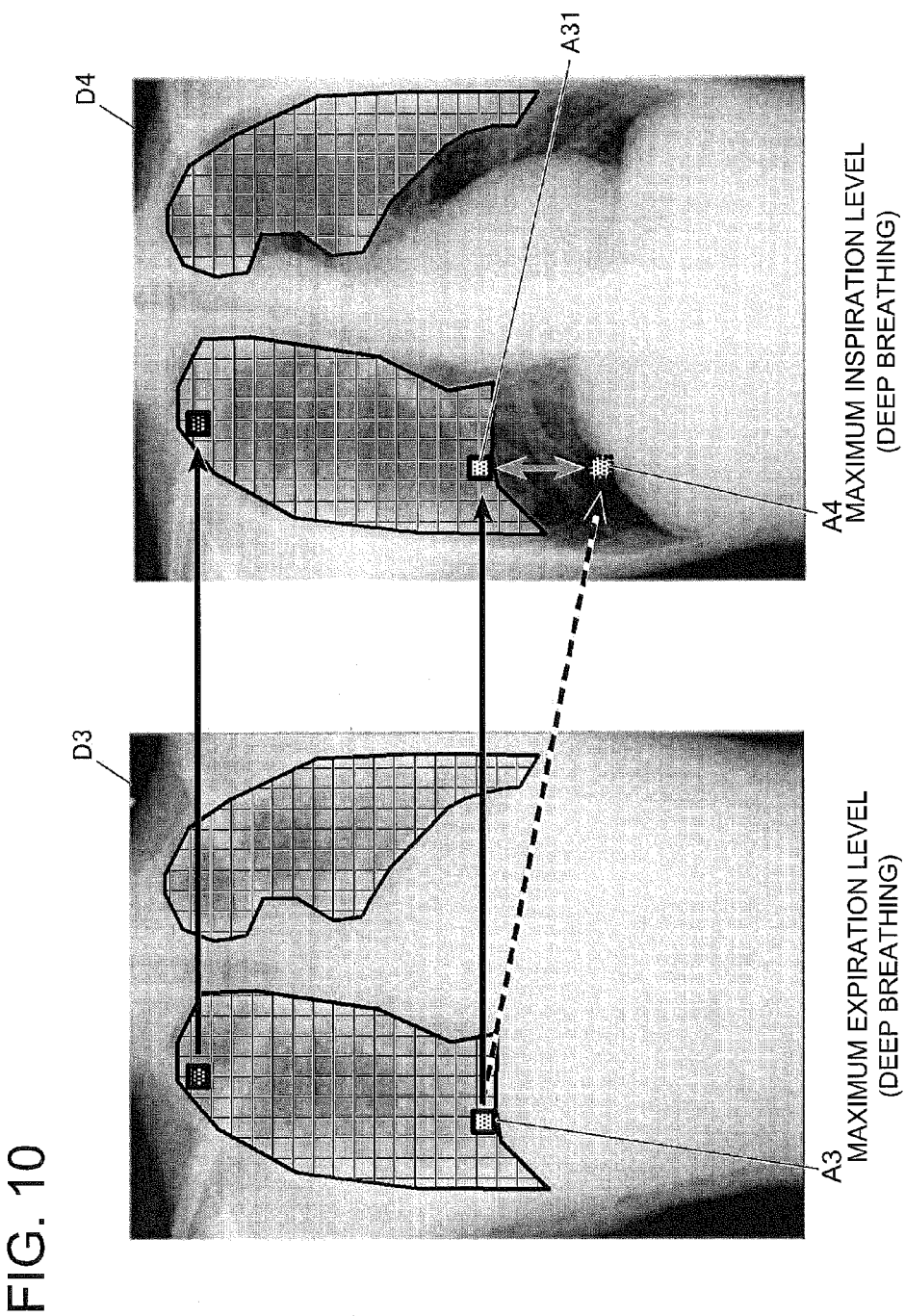
FIG. 10 is a figure showing changes of the positions of the area drawing the same portion of the lung field of a maximum inspiration level and a maximum expiration level.

The image at the maximum quiet expiration state can be obtained by extracting the image which has the position of the diaphragm in the highest position out of the series of frame images. By defining, in advance, for example, the reference position B1 of the diaphragm shown in FIG. 9 as an average position in the perpendicular direction of the curve C of the diaphragm (dotted line shown in FIG. 9), extracting the curve C of the diaphragm (lower end of the lung field area) from the lung field area R, and obtaining the average position in the perpendicular direction, the obtained position is specified as the reference position B1 of the diaphragm.

Subsequently, the signal value (average signal value) of the pixels in each small area of each frame image is calculated, output representing each small area is decided to an average signal value, and filtering processing of the direction of a time-axis is performed to each small area corresponded between each frame image (Step S103). The filtering processing is a processing for removing a high frequency signal change such as blood flow and extracting change of the signal value only by ventilation. For example, to the change of the signal value for each small area, the filtering processing performs a low pass filtering of the cutoff frequency of 0.5 Hz in the cutoff frequency for the quiet breathing image group, and the cutoff frequency of 0.7 Hz for the deep-breath image group. Here, the cutoff frequency of the low pass filter is preferable to be optimized for each radiographed motion image rather than to be set a fixed value. For example, the position of the diaphragm of the series of frame images is analyzed as mentioned above, in the case of quiet breathing, the frames which represent the positions of the quiet expiration state and the quiet inspiration state are detected, the time period of inspiration period is obtained from the number of frames between the frame of the position of the quiet expiration state and the frame of the position of the next quiet inspiration state, and the low pass filtering with the cutoff frequency which is represented by the value obtained by multiplying the reciprocal of the obtained the time period by the predetermined coefficient is performed. At this time, in the case of quiet breathing, the cutoff frequency set up automatically is preferable to be limited to 0.2-1.0 Hz. Further, in Step S1, a vital sign such as breathing rate and a pulse rate for one minute measured at a separate quiet time are input as patient information, and the cutoff frequency may be calculated from these values. For example, the breathing rate per one minute which was input as patient information may be changed into the breathing rate per one second, and a low pass filtering by making the value obtained by multiplying the breathing rate per one second by the predetermined coefficient into the cutoff frequency may be performed. Further, the input pulse rate per one minute may be changed into the breathing rate per one second, and a low pass filtering by making the average value of the breathing rate per one second and the cardiac beats rate per one second into the cutoff frequency may be carried out.

Subsequently, analysis is conducted for each small area which was corresponded in Step S102 of the series of frame images, and the feature amount of inspiration and the feature amount of expiration are calculated, respectively (Step S104). Here, the representative value (maximum of an absolute value) of the difference value (differentiation value) between neighboring frames for each small area in each of the expiration period and the inspiration period is calculated, for example, as the feature amount of expiration, and the feature amount of inspiration. The difference value between neighboring frames is a value which shows the amount of signal change. If the breathing causes the inspiration or the expiration, the thickness (density) of lungs will change according to the flow of the breath, and the amount of X ray penetrations (that is, signal value of pixel) will change with it. Therefore, it can be considered that the amount of signal change is a value which shows the airflow velocity in the timing. The representative value may be not limited to the maximum of the absolute value, but may be the median, the average value, or the modal value and so on.

Specifically, the difference processing between each neighboring frames which calculates the difference of the signal value in each small area between the frame images adjacent in the order of radiography (neighboring frame) is first performed. Here, for the frame images of the frame numbers N and N+1 (N is 1, 2, 3 . . . ), the difference value of "N+1−N" is calculated for each small area Subsequently, the maximum (maximum of absolute value) of the difference value between frames of the expiration period is obtained as the feature amount of expiration, and the maximum (maximum of absolute value) of the difference value between frames of the inspiration period is obtained as the feature amount of inspiration. The maximum (maximum of absolute value) of the difference value between frames is equivalent to the maximum differentiation value. Here, the period when the sign of difference value between frames in each small area is positive represents the inspiration period and the period when the sign is negative represents the expiration period.

Subsequently, the value of the ratio of the feature amount of the inspiration to the feature amount of expiration (feature amount of inspiration/feature amount of expiration) for each small area is calculated (Step S105). Here, "maximum of the difference value between frames of the inspiration period/ maximum of the difference value between frames of the expiration period" (it is called the maximum flow velocity ratio) is calculated.

Subsequently, while the histogram of the value of the "feature amount of inspiration/feature amount of expiration" for each calculated small area is created, the index value (here average value, standard deviation) which shows the tendency of the "feature amount of inspiration/feature amount of expiration" in the whole lung field is calculated (Step S106). The count number of the vertical axis of a histogram is desirable to be normalized by being divided by the number of all the small areas within a lung field Subsequently, the value of the "feature amount of inspiration/feature amount of expiration" calculated for each small area is converted into a parameter value for display based on the conversion table between the value of the "feature amount of inspiration/feature amount of expiration" and the parameter value at the time of display memorized in advance in the memory 32, and the image which displays each small area of the standard image (for example, frame image at the time of a maximum quiet expiration) is generated with the converted parameter value (Step S107). The conversion table is, for example, a table which corresponds with one to one between a threshold value (threshold value of each category) which specifies the range of the size of the feature amount of each category when classifying the feature amount into each category of normal/abnormalities (severity of illness 1-n), and any one of hue, brightness and luminosity, and transparency. Here, as the conversion table of the parameter values at the time of display, it is desirable that the threshold value of each category corresponds with hue in order to increase the identification ability to the size of the feature amount.

At this time, the display of high identification ability can be achieved by corresponding several hues (for example, 5-6 pieces) with the above-mentioned threshold value of each category and assigning middle hues to the values of the feature amount in-between (gradation is carried out).

The image colored based on the parameter values for display may be overlaid to the frame image of standard image.

Further, the conversion table corresponding to the motion image radiographed with grid and the conversion table corresponding to the motion image radiographed without grid are memorized in the memory 32. In Step S107 and the following step S108, whether the radiograph was taken with grid or without grid is judged based on the grid existence information associated with the series of frame images, and the coloring is performed using the conversion table corresponding to the judgment result.

And the created histogram, the generated still image and so on are displayed parallel on the display 34 (Step S108), and the breathing information generation processing is ended. Based on the conversion table of the above-mentioned value of "feature amount of expiration/feature amount of inspiration", and the parameter values at the time of display, the area of the histogram is colored and is displayed by same standard as each small area of the lung field area of the standard image.

Here, the influences on the motion state analysis when taking the radiograph with grid and when taking the radiograph without grid are explained.

Figure 11:
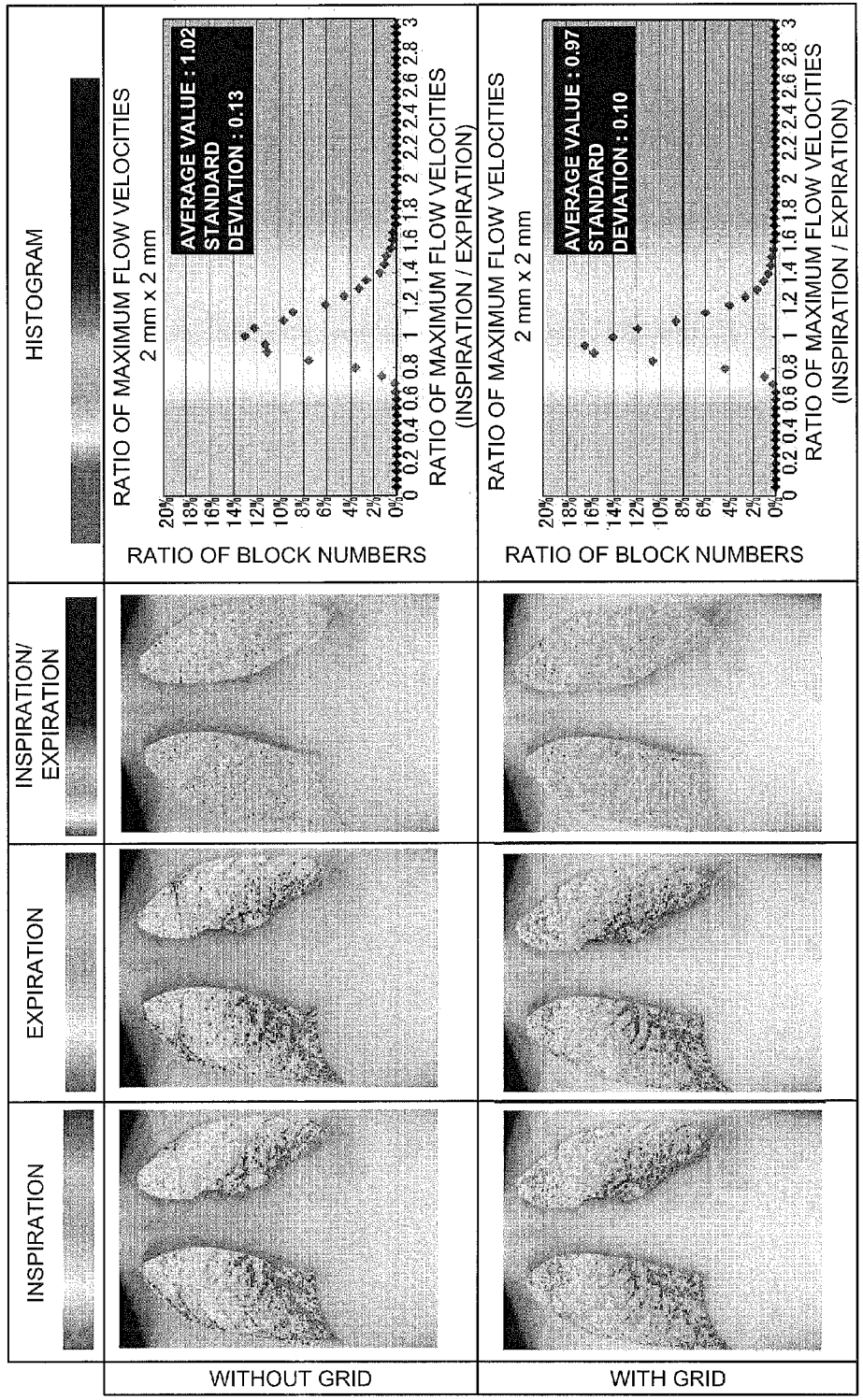
FIG. 11 is a figure showing a comparison of the motion state analysis results of the motion images which were taken a certain normal lung field with and without grid.

FIG. 11 is a figure showing a comparison of the motion state analysis results of the motion images when a certain normal lung field has been radiographed with grid and when the certain normal lung field has been radiographed without grid. In FIG. 11, the image which is colored based on "maximum of the difference value between frames of inspiration period" (the maximum inspiration airflow velocity), the image which is colored based on "maximum of the difference value between frames of an expiration period" (the maximum expiration airflow velocity), the image colored based on the maximum flow velocity ratio, and the histogram of the maximum flow velocity ratio, for each small area of the motion image radiographed with grid and without grid, are shown as the analysis result.

FIG. 11 shows the analysis result of the motion image which has been radiographed on the following radiography conditions.

The detector size is 40×30 cm, the detector pixel size is 194 micrometer, the grid pitch is 80 line/cm, the grid ratio is 12:1, the distance between detectors and the tube is 2 m, the frame number is 75 frames (radiographed during about 10 seconds), the total radiation dose (radiation dose to the radiographic subject when the radiation dose to the detector is made constant) with grid is 0.24 mGy, and the total radiation dose without grid is 0.14 mGy. Further the same conversion table (here conversion table for with grid) is used for the conversion table between the size and the color (shown in density in FIG. 11) of the maximum inspiration airflow velocity, the maximum expiration airflow velocity, and the maximum flow velocity ratio, in order to compare the both.

When imaging the same subject at the time of the motion image with grid and at the time of the motion image without grid, although the maximum inspiration airflow velocity, the maximum expiration airflow velocity, and the maximum flow velocity ratio are almost equivalent, as shown in FIG. 11, a little difference may arise according to the feature and so on of the radiography system. For example, the form of the histogram of the motion image radiographed without grid in FIG. 11 has a broader form compared with the histogram of the motion image radiographed with grid. Therefore, it is not desirable that the classification to different color display, i.e. different severity of illness even for the same maximum flow velocity ratio may be made, when the same threshold value (conversion table) for both the cases with grid and without grid is used when classifying and coloring the area within the lung field and the area of the histogram into, for example, normality, abnormalities of the category of 1-n, according to the maximum flow velocity ratio. Then, as shown in FIG. 11, when the difference which influences diagnosis arises for the cases with grid and without grid, it is necessary to change the threshold value (conversion table) used for the classification of the feature amount according to the grid existence.

How much difference arises between the result of having analyzed the motion image radiographed with grid, and the result of having analyzed the motion image radiographed without grid, depends on the feature of the radiography system, the contents of analysis and so on. Therefor; it is preferable to analyze plural images which have been obtained by radiographing the same radiographic subject with grid and without grid by the radiography system, and calculate, by induction, the threshold value used for motion image with grid and the threshold value used for motion image without grid, by using the result.

In addition, it can be considered that it is also enough if the threshold value for motion images taken without grid is memorized since radiography equipment 1 is controlled to take a motion image without grid in the embodiment. However, the case that the console for diagnosis 3 is connected to the radiography system which can take motion image with grid may be assumed. In this case, the judgment will be mistaken when the radiography conditions with grid and without grid differ. Then, in the embodiment, the grid existence information is attached to the incidental information on each frame image which constitutes the motion image, and the analysis is performed by the control section 31 based on the grid existence information and with the analysis algorithm using the threshold value according to the grid existence at the time of radiography.

Figure 12B:
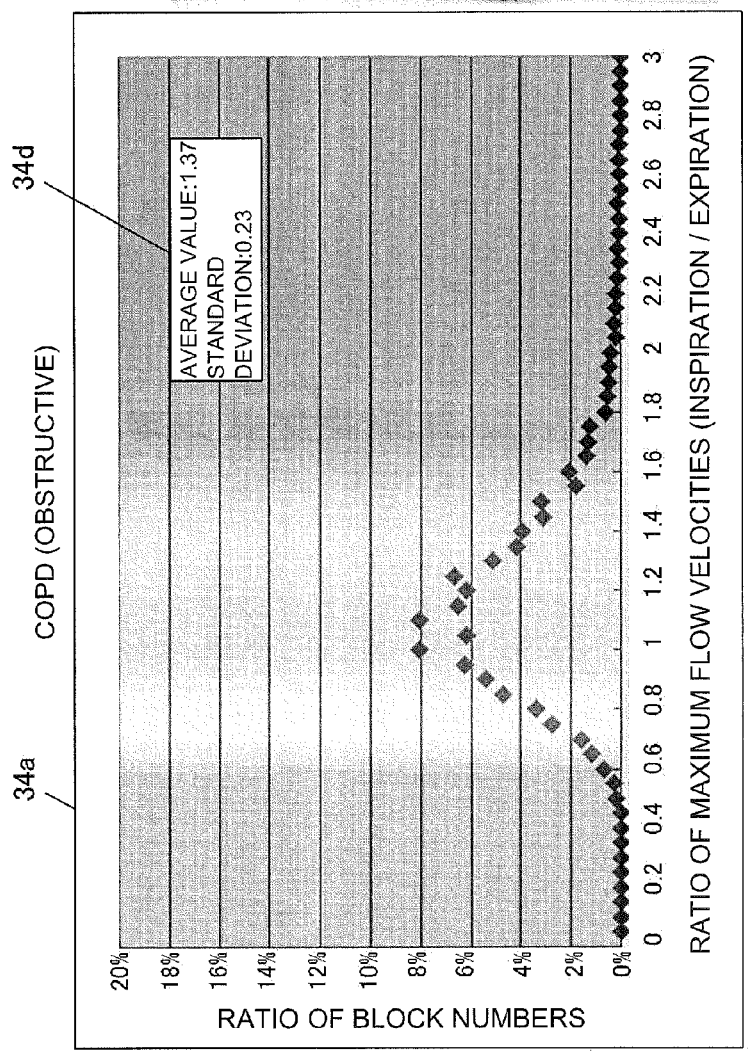
FIG. 12B is a figure showing an example of the display screen which displays the analysis result obtained by analyzing the motion image of the lung field of COPD (obstructive disease)
Figure 12C:
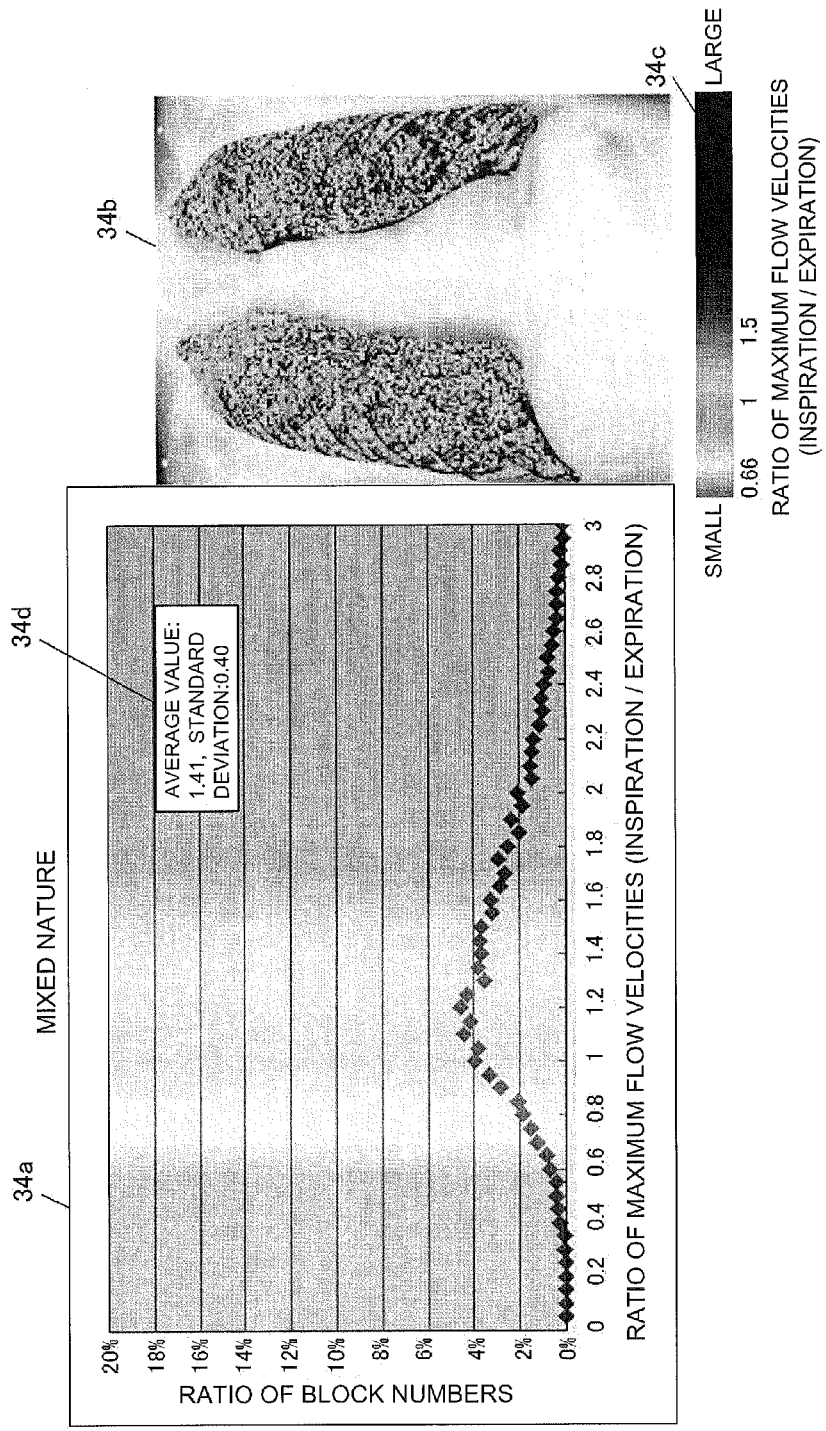
FIG. 12C is a figure showing an example of the display screen which displays the analysis result obtained by analyzing the motion image of the lung field of a mixed obstructive and restrictive lung disease.

The examples of the display screen displayed on the display 34 in Step S108 are shown in FIGS. 12A-12C.

FIG. 12A shows the display screen which display the analysis result (diagnosis support information relating to breathing) of having analyzed the motion image of lung field of the normal person radiographed with grid. FIG. 12B shows the display screen which displays the analysis result having analyzed the motion image of the lung field of COPD (obstructive disease). FIG. 12C shows the display screen which displays the analysis result of having analyzed the motion image of the lung field of a mixed obstructive and restrictive lung disease.

As shown in FIGS. 12A-12C, in Step S108, the histogram 34a of the value of the "feature amount of inspiration/feature amount of expiration" of each small area (square size of 2 mm) in the lung field area extracted from the frame image of 14×17 inch size, the still image 34b which shows the "feature amount of inspiration/feature amount of expiration" of each small area by list, the display 34c which shows the relation between the hue currently displayed with the histogram 34a and the still image 34b and the value of the "feature amount of inspiration/feature amount of expiration", and the index value 34d which indicates the tendency of the "feature amount of inspiration/feature amount of expiration" in the whole lung field are displayed. Further, as shown in FIGS. 12A-12C, the histogram 34a is displayed by classifying the area of the horizontal axis by color with six hues, according to the size of the value of the "feature amount of inspiration/feature amount of expiration". Thereby, the doctor can recognize the distribution of the "feature amount of inspiration/feature amount of expiration" within the lung field easily only by a glance at the histogram. Further, since each small area is classified by color and displayed by the same standard as the classification by color of the histogram according to the value of the "feature amount of inspiration/feature amount of expiration" in the still image 34b which shows the "feature amount of inspiration/feature amount of expiration" of each small area, the doctor can recognize easily the regional unusual portion within the lung field (obstructive portion, restrictive portion). Furthermore, as the index value 34d which shows the tendency of the "feature amount of inspiration/feature amount of expiration" in the whole lung field, it is possible to provide the doctor with the tendency of the "feature amount of inspiration/feature amount of expiration" in the whole lung field as a numerical value, by calculating the average value and standard deviation and displaying collectively them on the screen.

When the maximum (absolute value) of the difference value between frames of expiration period is regarded as the feature amount of expiration, and then maximum (absolute value) of the difference value between frames of inspiration period is regarded as the feature amount of inspiration, it is known that the average value of the "feature amount of inspiration/feature amount of expiration" of the whole lung field is in about 0.94.2, and the standard deviation is in about 0.10-0.22, in the lung field of the normal person, when the analysis is performed by the motion image taken by motion imaging with grid. Therefore, the doctor can recognize easily that the radiographed lung field is normal, when the display screen shown in FIG. 12A at Step S108 is displayed.

On the other hand, in the lung field of COPD (obstructive disease), when the analysis is performed by the motion image taken by motion imaging with the grid, it is known that the average value of the "feature amount of inspiration/feature amount of expiration" of the whole lung field is not in 0.9-1.2

(larger compared with the normal person), and the standard deviation is not in 0.10-0.22 (large compared with the normal person), either. Therefore, when the display screen shown in FIG. 12B at Step S108 is displayed, the doctor can recognize easily that the radiographed lung field is of COPD.

On the other hand, when analyzing by the motion image which has been taken by motion imaging with grid, it is known that, for the lung field of the mixed obstructive and restrictive lung disease, both the number of data of 0.66 or less and the number of data of the 1.5 or more in the value of the "feature amount of inspiration/feature amount of expiration" of the whole lung field increase. Therefore, when the display screen shown in FIG. 12C at Step S108 is displayed, the doctor can recognize easily that the radiographed lung field is of the mixed obstructive and restrictive disease.

Thus, in the chest diagnostic support information generation system 100, it is possible to provide the doctor with useful diagnostic support information which can specify illness states, severities of illness and so on such as uneven ventilation of COPD (obstructive pulmonary disease), and mixed obstructive and restrictive lung disease, from the index value which shows the tendency of the "feature amount of inspiration/feature amount of expiration".

The normality or abnormality of the radiographic subject M may be judged by using the index value which shows the tendency of the "feature amount of inspiration/feature amount of expiration". In this case, it is preferable to change the threshold value for judging the normality or abnormality based on the grid existence information. For example, when judging the normality or abnormality based on the average value of the "feature amount of inspiration/feature amount of expiration" of the above-mentioned whole lung field, it is preferable to judge that average value 0.9-1.2 with grid is regarded as normal and average value 0.8-1.3 without grid is regarded as normal.

As the feature amount of expiration, and the feature amount of inspiration, other feature amounts than the above-mentioned examples may be used.

For example, the feature amount of expiration may be represented by the number of frame images equivalent to one expiration period (expiration time) of one cycle of breathing, and the feature amount of inspiration may be represented by the number of frame images equivalent to the inspiration period (inspiration time) of one cycle of breathing. Here, when the ventilation function of the lungs is normal, the expiration period and the inspiration period should become almost the same length or the expiration period should become longer a little than the inspiration period. Therefore, the doctor can recognize whether there is any doubt of the lung disease, by glancing the value of "the number of frame images equivalent to the expiration period/the number of frame images equivalent to the inspiration period". Especially, the area of "the number of frame images of expiration period/the number of frame images of inspiration period">1.5 can be regarded as the obstructive portion where the ventilation is difficult to be carried out by taking air and discharging air taken is delayed. Further, since the relation of "maximum value of difference value between frames of inspiration period/maximum value of difference value between frames of expiration period≈expiration period (number of frame images of expiration)/inspiration period (number of frame images of an inspiration)" is realized, the doctor can identify the normality, COPD (obstructive pulmonary disease), and the mixed obstructive and restrictive lung disease by the same criterion of judgment as the case where the feature amount of expiration is regarded as the maximum of the difference values between frames of expiration period and the feature amount of inspiration is regarded as the maximum of the difference values between frames of the inspiration period.

Further, in each frame image for one breathing cycle, it is also preferable to calculate the signal value (average signal value) of the pixel of each small area, calculate the minimum and maximum of the signal value in one cycle breathing for each small area, and regard the calculated minimum as the feature amount of inspiration and the calculated maximum as the feature amount of the expiration for the area. It can be understood that the difference of the maximum and the minimum of the signal value becomes large in the normal portion, and the difference becomes very small in the abnormal portion. This is because the motion of alveoli worsens and the density change of alveoli becomes small in the abnormal portion. Therefore, by checking the average value and the standard deviation with reference to the histogram of "the maximum of the signal value/the minimum of the signal value", the doctor can regard it as the judgment material whether the lung field is normal or is abnormal. For example, when the average value of "the maximum of the signal value/the minimum of the signal value" of the whole lung field is larger than 1 and the standard deviation is small, it can be judged that the function of lungs is normal. On the other hand, when the average value of "the maximum of the signal value/the minimum of the signal value" of the whole lung field is near 1, and the standard deviation is large, it can be judged that there is a disease in the lung function.

In addition, as the index value which shows the tendency of the "feature amount of inspiration/feature amount of expiration", the value of the "feature amount of inspiration/feature amount of expiration" where the count number (the number of blocks (small areas)) other than the average value and the standard deviation, becomes a peak of the histogram, the count number (the number of blocks) or a ratio of the count number when the value of the "feature amount of inspiration/feature amount of expiration" becomes less or more than a predetermined value, can be served. Or a new index value may be created by combining these plural index values.

Figure 13:
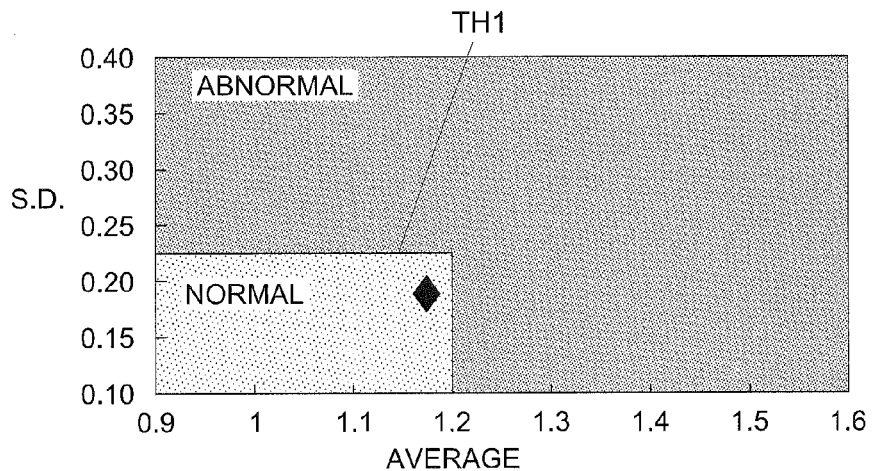
FIG. 13 is a figure showing an example of a display of the index value which shows the tendency of the "feature amount of inspiration/feature amount of expiration"

As shown in FIG. 13, for example, by showing a threshold value TH1 between normality and abnormalities for each index value in the graph in which the X-axis represents one of the index values which show the tendency of the "feature amount of inspiration/feature amount of expiration" and the Y-axis represents another, the figure where the index value which shows the tendency of the "feature amount of inspiration/feature amount of expiration" in the whole lung field calculated from the motion image is plotted on the graph can be considered as an analysis result. FIG. 13 is the graph in which the X-axis represents the average value of "maximum of the difference values between frames of inspiration period/maximum of the difference value between frames of expiration period", the Y-axis represents the standard deviation, and index values for the average values and the standard deviations of the "feature amount of inspiration/feature amount of expiration" in the whole lung field calculated from the motion image are plotted. By displaying the index values which show the tendency of "the feature amount of inspiration/feature amount of expiration", the grade of abnormalities becomes easily recognized according to the distance from the plotted points to the threshold value TH1.

Figure 14:
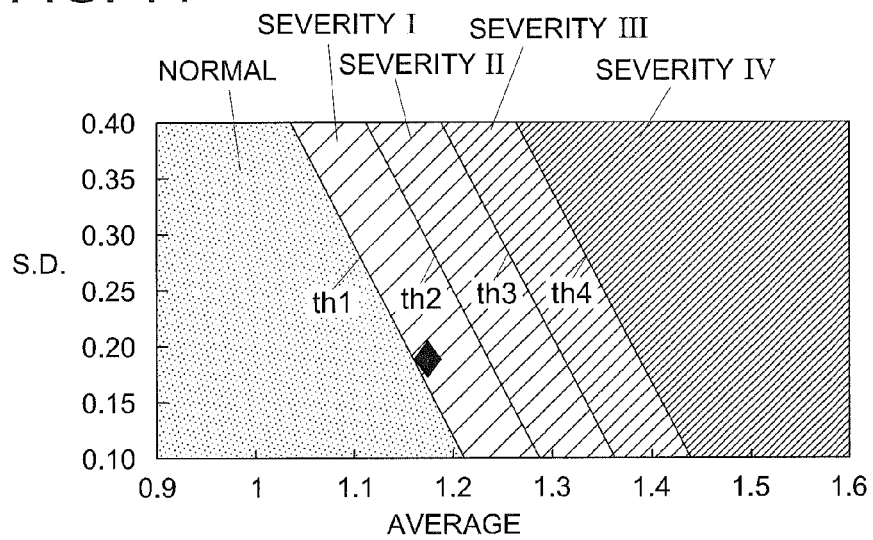
FIG. 14 is a figure showing an other example of a display of the index value which shows the tendency of the "feature amount of inspiration/feature amount of expiration"

Further, a value obtained by carrying out a linear combination of two index values (for example, average value of the "feature amount of inspiration/feature amount of expiration", standard deviation) is set to a new index value. As shown in FIG. 14, the threshold values th1-th4 for classifying the new index value (index value obtained by carrying out the linear combination of the two index values) according to the severity of illness may be shown on the graph which set the X-axis to one of the two index values and the Y-axis to the other of the two index values, and the new index value calculated from the motion image may be plotted on this graph. As an example of the linear combination, the 1st main component calculated by a main component analysis from a large number of the measured value data to the average value and the standard deviation can be set as the index value. By using such the graph, the grade of abnormalities becomes visually recognized more easily. Further, for example, the first main component may be calculated by computing the maximum feature value of the covariance procession to N×M data from the measured large number of value data (number N) to plural the index values (number M), and the calculated main component may be used as the index value.

Figure 15:
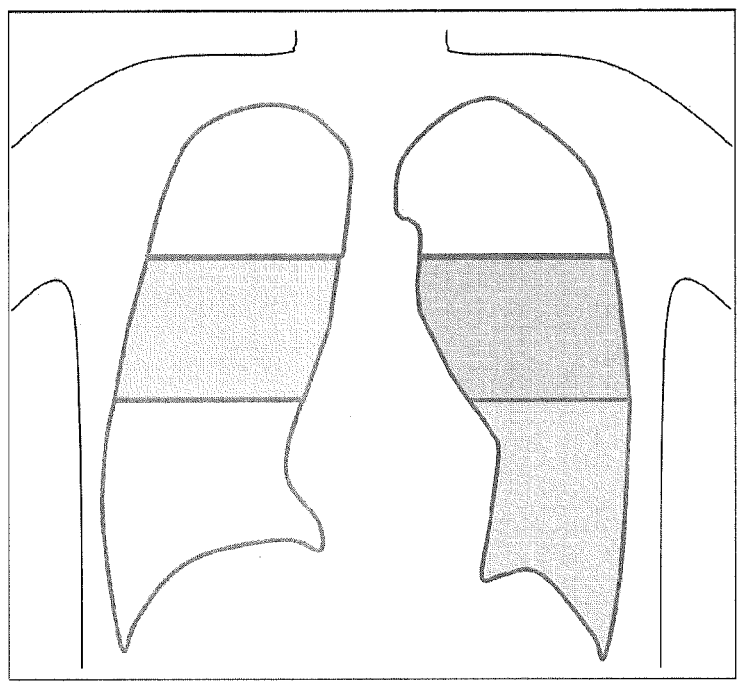
FIG. 15 is a figure showing the example of a display of the index value which shows the tendency of the feature amount of the inspiration or the feature amount of the expiration.

Further, other than the index value which shows the tendency of the "feature amount of inspiration/feature amount of expiration", the index values which show respectively the tendency of the feature amount of inspiration or the tendency of the feature amount of expiration may be calculated. For example, as shown in FIG. 15, to the feature amount of inspiration or the feature amount of expiration calculated for each small area, a coefficient of variation (=standard deviation/average value) in each of a total of six portions which is obtained by dividing insides of the right lung field and the left lung field respectively into three portions of an upper, a middle and a lower portions may be calculated, and the still image which colors and displays the six areas by the hue (or luminosity or chroma saturation) according to the size of the coefficient of variation may be created. By giving such display, it becomes easy to recognize the distribution of unequal ventilation, and it becomes easy to judge whether the portion where the unequal ventilation is performed is sectional or diffused.

Next, the blood flow information generation processing performed in Step S24 of FIG. 5 is explained.

Figure 16:
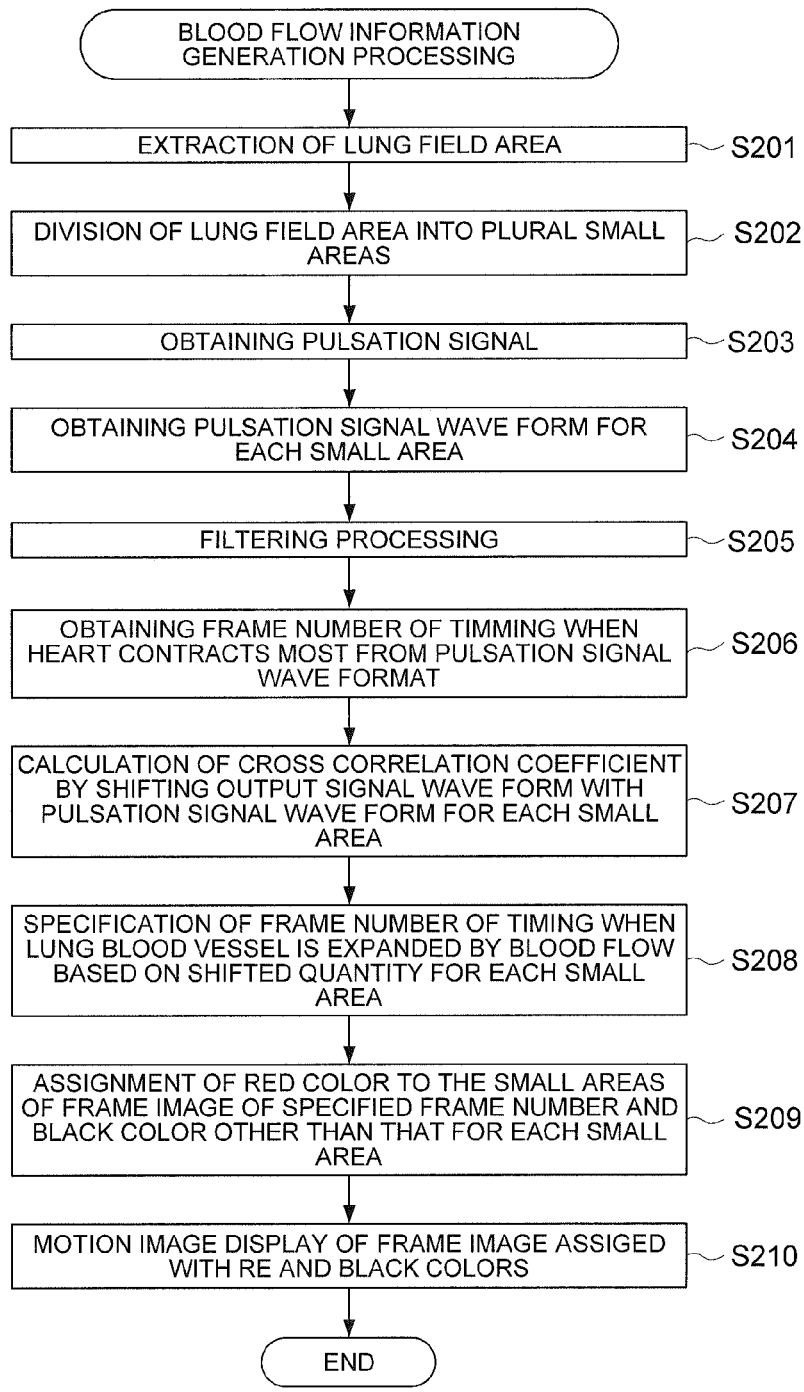
FIG. 16 is a flow chart which shows the blood flow information generation processing performed by the control section of the console for diagnosis of FIG. 1.

The flow chart of blood flow information generation processing is shown in FIG. 16.

In the blood flow analysis in the embodiment here, as the lung field blood vessel expansion is caused when blood is rapidly discharged out through the main artery from the right ventricle by the contraction of the heart, the lung field blood vessel expansion is extracted by analyzing the motion image and is output as diagnostic support information relating to blood flow. That is, as shown in FIG. 17, since when the blood vessel is expanded in the lung field (alveoli area), the amount of radiation penetrations of the area where the lung blood vessel expands will decrease comparatively more largely than the amount of radiation penetrations where the blood vessel is not expanded, the output signal value of the radiation detector 13 corresponding to this area decreases. Such the expansion of the lung blood vessel in response to the pulsation of the heart transmits from the artery near the heart to peripheries. Then, the each pixel of the radiation detector 13 between the series of frame images which constitute the motion image, or the each small area (aforementioned block) each of which consists of plural pixels is corresponded with each other and the frame image of which the signal value becomes the lowest for each pixel or small area is sought, and the corresponding area of the frame image is colored as the signal which shows the timing when the lung blood vessel is expanded by the blood flow. And the doctor can visually recognize the state of the blood flow by displaying the series of frame images after the coloring on the display 34 sequentially.

Figure 18A:
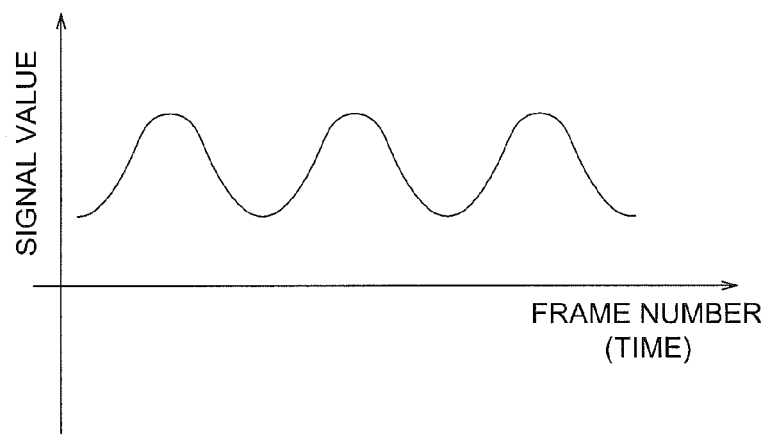
FIG. 18A is a figure showing schematically a normal output signal waveform.
Figure 18B:
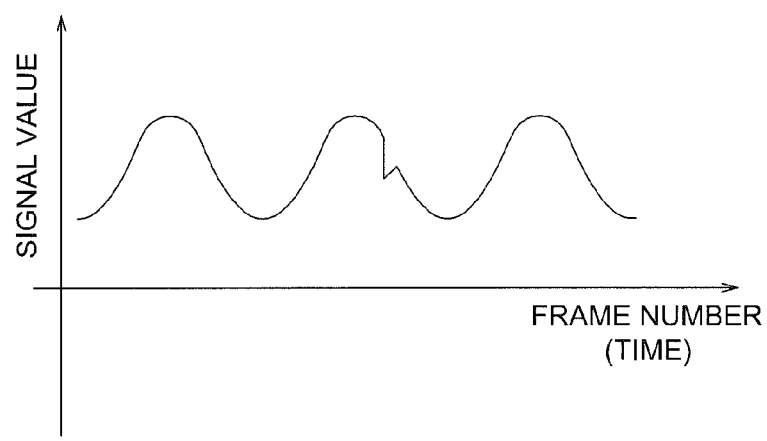
FIG. 18B is a figure showing schematically an output signal waveform with an abnormal portion.

As shown in FIG. 18A, the signal (it is called blood-flow signal) which shows the timing when the lung blood vessel is expanded by the blood flow in each pixel (small area) can be acquired by calculating the minimum value of the waveform (it is called output signal waveform) which shows the change of the signal value of the pixel (small area). Although this blood-flow signal appears at the same interval as the pulsation cycle of the heart, as shown in FIG. 18B such as abnormal heart rhythm, if there is an unusual portion, the minimum value may appear at a different interval from the pulsation cycle of the heart regardless of the expansion of the blood vessel accompanying the blood flow. Then, in the embodiment, it is possible to extract the blood-flow signal with a sufficient accuracy by seeking the correlation coefficient of the pulsation signal waveform which shows the pulsation of the heart and the output signal waveform of each small area.

In the blood flow information generation processing, the lung field area is first extracted from each frame image (Step S201). The explanation about the extraction of the lung field area is the same as that of what was explained at Step S101 of FIG. 6, and is applicable here.

Subsequently, the lung field area of each frame image is divided into the small areas each of which consists of plural pixels, and the small area of each frame image is corresponded with each other (Step S202). The explanation about division of the small area of the lung field area, and the corresponding of each small area between neighboring frame images is the same as that of what was explained at Step S102 of FIG. 6, and is applicable here. Further, the signal value for each small area is transposed to the representative value (average value, the median, a mode, and so on).

In addition, processing may not be performed in each small area but in each pixel hereafter, without processing Step S202.

If the size of the small area is enlarged, a certain periodic change will appear in the output signal value (representative value) of each small area. However that will contain the noise by the above-mentioned breathing cycle. Further, if the size of the small area becomes large, the rate of the influence of the expansion of the blood vessel occupying the integrated value of each small area will decrease, the periodic detection accuracy of the expansion of lung blood vessel will decrease gradually, and it will be difficult. Further, by considering the visibility which includes the afterimage effect of the user (doctor) who observes the motion image (page turning over display image) in which the blood flow is visually recognizably displayed at Step S210 mentioned later, the size of the small area in this invention is preferably 0.2-5 mm, and is more preferably 0.4-2 mm.

Subsequently, the pulsation signal waveform used as the reference at the time of extracting the blood-flow signal is obtained (Step S203).

As the pulsation signal waveform, any of the following may be used:

(1) Waveform which shows the time change of the signal value in the ROI (Region of interest) which is designated in the heart region (or main artery area).

(2) Signal waveform obtained by reversing the waveform of (1)

(3) Cardiac signal waveform obtained from electrocardiographic sensor (4) Signal waveform which shows the motion (change of the position) of heart wall That is, in the chest diagnostic support information generation system 100, any of sections above-mentioned (1)-(4) by which the pulsation signal waveform is obtained is provided. Further, in the case of the configuration of using the cardiac signal waveform by the electrocardiographic sensor as the pulsation signal waveform, while the frame image is obtained by motion imaging, the cardiac signal waveform by the electrocardiographic sensor is obtained, and is memorized in RAM. In Step S203, the cardiac signal waveform memorized in RAM is read out. Further, it is ideal to set ROI of the heart region in the right ventricle area, however it may be set in the left ventricle area. This is because the extraction of the signal waveform is easy in the left ventricle area than in the right ventricle, and the cardiac-beat cycle in the right ventricle area is almost the same as in the left ventricle, in the motion imaging. However, when using the left ventricle for the pulsation signal waveform, the blood vessel expansion timing may be compensated by such a method of adding the timing difference of the cardiac-beats cycle between of the right ventricle and the left ventricle, as an amount of offset, to the blood vessel expansion timing calculated by the method of mentioning later.

Figure 19:
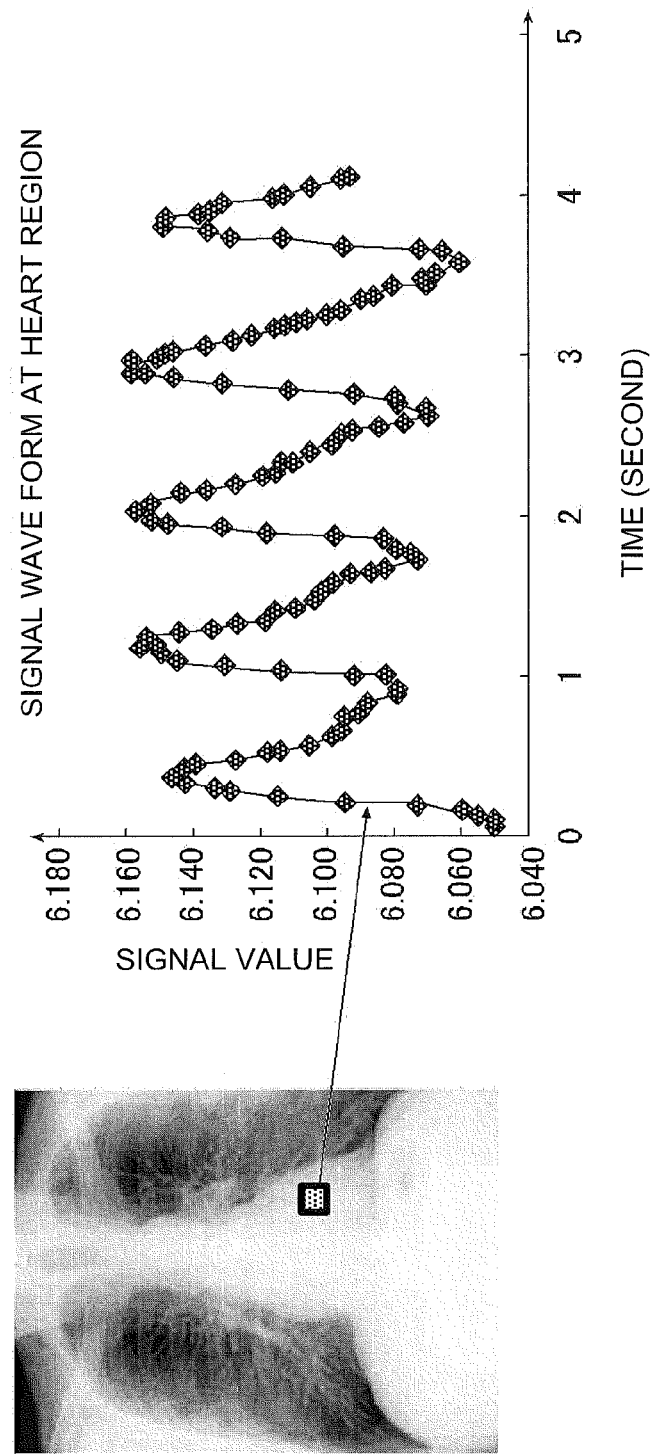
FIG. 19 is a figure showing an example of a pulsation signal waveform.

As shown in FIG. 19, the signal waveform mentioned above (1) can be created by plotting the signal value (representative value) of the ROI region of each frame image on the coordinate space of which the horizontal axis represents the lapsed time (frame number) from the radiography start of the motion image and the vertical axis represents the signal value in the ROI (representative value), for the ROI region specified by the operation section 33.

Figure 20:
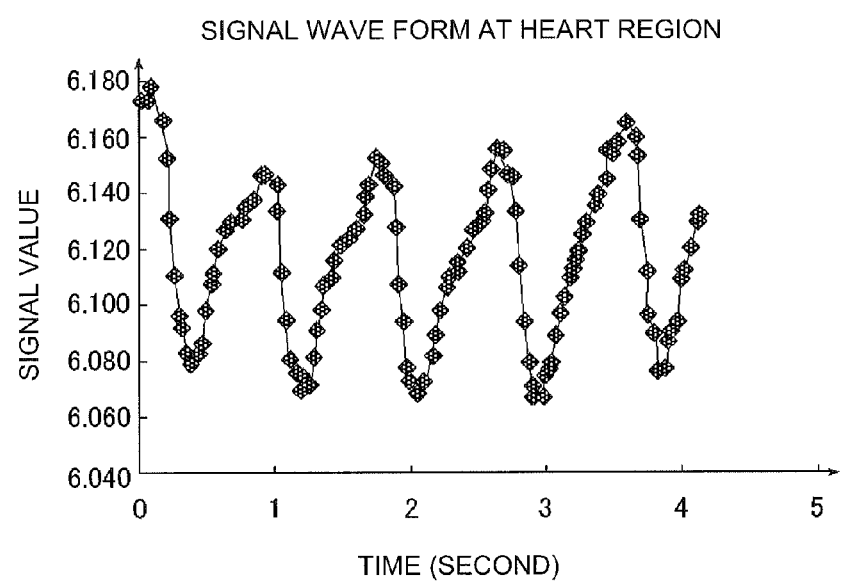
FIG. 20 is a figure showing an example of a reversed pulsation signal waveform.

As shown in FIG. 20, (2) is the wave form obtained by reversing the signal waveform of (1). This waveform is made into the approximate form of the signal waveform of each small area (or each pixel), and makes the calculation of the cross correlation coefficient in a following step easy.

Figure 21A:
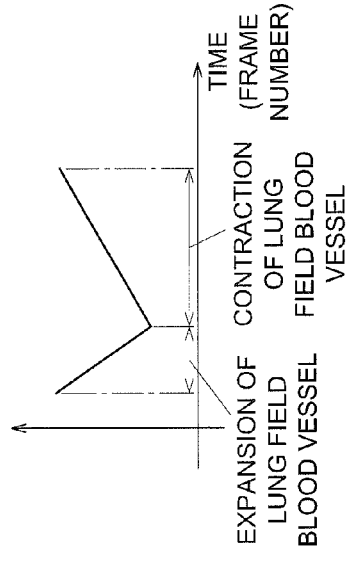
FIGS. 21A, 21B, 21C and 21D are figures for explaining the reason for reversing the pulsation signal waveform.
Figure 21B:
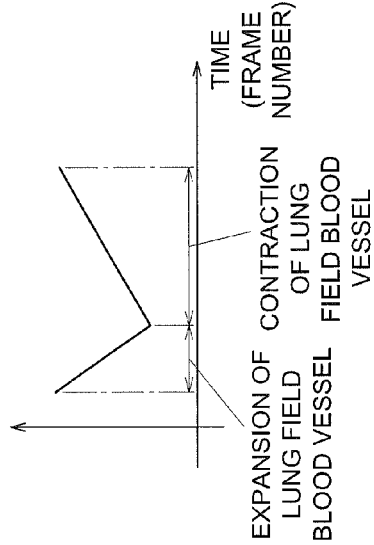
Figure 21C:
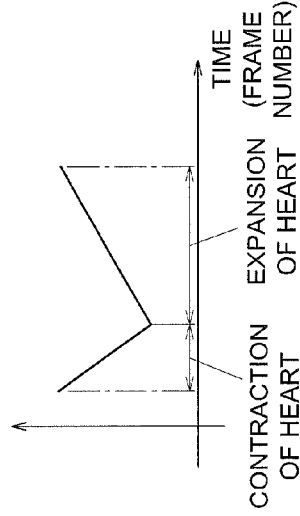
Figure 21D:
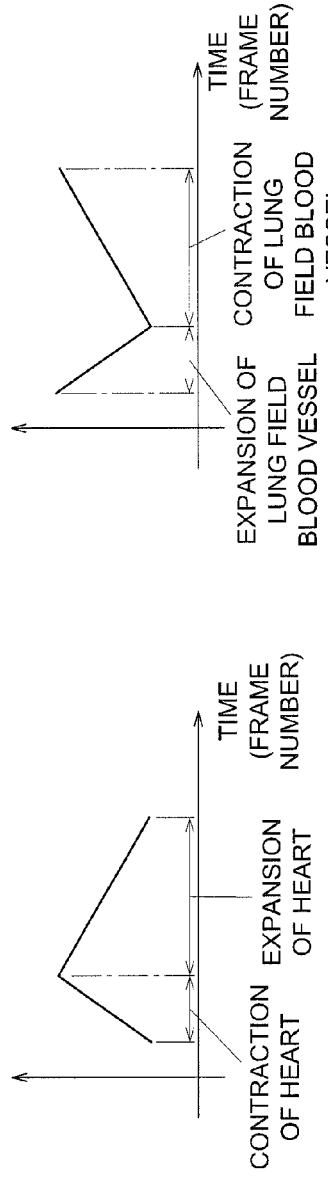

FIG. 21A shows typically the output signal waveform of ROI which is set at the heart region for one cardiac beat, and FIG. 21B is the figure showing typically the output signal waveform of the lung blood vessel area for one cardiac beat. As shown in FIG. 21A, since blood is discharged rapidly from the ventricle into the main artery by contraction of the heart, the signal value of ROI increases rapidly during the contraction period of the heart (ventricle), however the signal value of the output signal waveform of ROT in one cardiac beat decreases gently since the heart is expanded by the gentle inflowing of blood from the blood vessel during the expansion period of the heart (ventricle). On the other hand, in the lung field blood vessel, as shown in FIG. 21B, the signal value decreases rapidly corresponding to the contraction period of the heart, since the blood vessel wall is expanded by the inflowing of the blood rapidly discharged from the heart by the contraction of the heart. During the contraction period of the lung field blood vessel, the signal value increases, since the blood vessel wall contracts by the gentle discharge of the blood to the heart. Thus, the output signal waveform of the lung field blood vessel area is the one reversing the output signal waveform of the heart region. Then, as shown in FIG. 21C and FIG. 21D, the both features of the forms of the signal waveforms are aligned by reversing the output signal waveform of the heart region.

The signal waveform of (4) can be created by plotting the reference position of the heart wall position of each frame image on the coordinate space of which horizontal axis represents the lapsed time (frame number) from the radiography start of the motion image and vertical axis represents the reference position (y-coordinate) of the heart wall position, by recognizing the heart region by a template matching and so on in each frame image, and specifying the reference position (for example, (outside) edge point in the heart region where the x-coordinate (horizontal coordinates) is the largest) of the heart wall position.

Subsequently, the waveform (output signal waveform) which shows the time change of the signal value of the small area is generated for each small area (Step S204). The output signal waveform for each small area is generated by plotting the representative value of the small area of each frame image on the coordinate space of which the horizontal axis represents the lapsed time (frame number) from the radiography start of a motion image, and the vertical axis represents the signal value (representative value of the output signal value of the radiation detector 13, for example, the average value, the median, a mode, and so on).

Subsequently, the filtering processing in the direction of time axis is performed to the pulsation signal waveform and the output signal waveform of each small area (Step S205).

This filtering processing is the processing for removing the signal change of the low frequency wave according to the breathing and so on, and extracting change of the signal value by the blood flow. For example, the high pass filtering of the low region cutoff frequency of 0.7 Hz for the quiet breathing image group and the low region cutoff frequency of 0.5 Hz for the deep-breath image group is performed to the time change of the signal value for each small area. Or, in order to remove the noise component of the further higher frequency, filtering with the band path filter which also cuts the further high frequency with the high region cutoff frequency of 4.5 Hz may be performed.

Here, as for the above-mentioned cutoff frequencies, it is more preferable to optimize them for each radiographed motion image rather than to set them to fixed values. For example, the time of the contraction period of the heart and the time of expansion period (relaxation term) are calculated from the signal change of the heart region of the series of frame images as mentioned above. And the value which is obtained by multiplying the reciprocal of the time of expansion period by the predetermined coefficient is set as the cutoff frequency with which the high pass filter or the band pass filter cuts off the low frequency waves. Further, in the case of the band pass filter, the value which is obtained by multiplying the reciprocal of the time of the contraction period by the predetermined coefficient is set as the high region cutoff frequency which cuts off the high frequencies. Furthermore, for low region cutoff frequency, the value of the diaphragm from the series of frame images is analyzed in consideration of the frequency component by breathing, the frame images of the quiet inspiration and the quiet expiration in the case of resting ventilation are detected, the time of inspiration period is obtained from the number of frames between the frame of the quiet expiration and the frame of the next quiet inspiration, and the value calculated by multiplying the reciprocal of the obtained time of inspiration period and the average value of the time of the above-mentioned expansion period with the predetermined coefficient may be set as the low region cutoff frequency. In the case of quiet breathing, as for the cutoff frequencies automatically setup, the low region cutoff frequency is preferable to be restricted to 0.2-1.0 Hz and the high region cutoff frequency is preferable to be restricted to 2.0 Hz or more. Further, in Step S1 of FIG. 4, after vital signs, such as the breathing rate separately measured for one minute at the quiet time and the pulse rate are input as patient information, the cutoff frequency may be calculated from these values.

For example, by converting the breathing rate for one minute which has been input as patient information into the breathing rate for one second, the value obtained by multiplying the breathing rate by the predetermined coefficient may be regarded as the low region cutoff frequency. Further, by converting the pulse rate for one minute which has been input as patient information into the pulse rate for one second, the value obtained by multiplying the pulse rate for one second by the predetermined coefficient may be regarded as the high region cutoff frequency. Furthermore, the value obtained by multiplying the average value of the breathing rate for one second and the cardiac beats rate for one second by the predetermined coefficient may be set as the low region cutoff frequency.

Further, the filtering processing in Step S205 is carried out for extracting the blood-flow signal accurately and may be omitted depending on the required accuracy and the processing speed. Although the lung blood vessel position with respect to each small area is not always constant and moves with breathing, when the lung blood vessel goes out from the small area, the signal value of the small area will become greater. Since the breathing cycle of the lung field is about 2-10 seconds, the cycle of the radiograph of the lung blood vessel to each small area also follows the breathing cycle. Further, the rib position also moves in accordance with the breathing cycle, and the signal value of each small area is affected. However, since the pulsation cycle of the heart is very short compared with the breathing cycle, it becomes possible to obtain the blood-flow signal by using the periodic difference even for the data (image which has not been performed filter processing) on which each above-mentioned component superimposes.

Subsequently, the number of the frame image of the timing when the heart contracts most is obtained from the pulsation signal waveform subject to the filtering processing (Step S206). For example, when using the reversed signal waveform in ROI explained by above-mentioned (2) as the pulsation signal waveform, the local minimum value of the wave form (frame image from which the signal value serves as the minimum, frame numbers 8 and 16 in FIG. 22A) is the frame image of the timing when the heart contracts most.

Subsequently, the cross correlation coefficient with the pulsation signal waveform is calculated for each small area, with shifting then output signal waveform by one frame interval (shifting in the direction of time) (Step S207).

For example, first, the cross correlation coefficient of two signal waveforms of the pulsation signal waveform and the output signal waveform of the same time-axis where the frame numbers from the radiography start are mutually in agreement is calculated (the cross correlation coefficient without a time shift is calculated). Subsequently, the cross correlation coefficient of two signal waveforms by shifting the output signal waveform to the left by one frame with respect to the pulsation signal waveform, i.e. advancing by one-frame interval, is calculated. Hereafter, the shift to the left of the output signal waveform is repeated, and the cross correlation coefficient where the output signal waveform to each small area is respectively shifted more than one cardiac beat cycle to the left from the position without shifting is calculated. Subsequently, similarly, the cross correlation coefficient where the output signal waveform is shifted more than one cardiac beat cycle to the right from the position without shifting while shifting the output signal waveform to the right one frame by one frame may be calculated. However, since the phase of the output signal waveform is usually delayed in terms of time to the pulsation signal waveform extracted from the heart, it is sufficient to calculate only the shift to the left which specifies the delay degree. However, since the number of data used for the cross correlation coefficient calculation decreases by the shifting the output signal wave form, the calculation accuracy of the cross correlation coefficient decreases by the decreasing of the number of data according to the shift amount. Then, by regarding the pulsation signal waveform and the output signal waveform as perfect periodic functions, the cross correlation coefficient may be calculated to the case of shifting to the left from the position without shifting to more than ½ cardiac beat cycle, as well as, to the case of similarly shifting to the right from the position without shift to more than ½ cardiac beat cycle, and the cross correlation coefficient to the shifting to the right may be regarded as the cross correlation coefficient to the case of shifting to the left by the number of frames which are equal to the subtraction of the number of the shift to the fight from the number of frames corresponding to one cardiac beat cycle. By doing in this way, the decrease of the number of data according to the shift amount at the time of the cross correlation coefficient calculation can be suppressed. The cross correlation coefficient can be calculated by following [Equation 1].

$$C = \frac{1}{J}\sum_{j=1}^{J} \frac{\{A(j)-m_A\}\{B(j)-m_B\}}{\sigma_A \sigma_B} \quad [\text{Equation 1}]$$

$$m_A = \frac{1}{J}\sum_{j=1}^{J} A(j), \; m_B = \frac{1}{J}\sum_{j=1}^{J} B(j)$$

$$\sigma_A = \sqrt{\frac{1}{J}\sum_{j=1}^{J} \{A(j)-m_A\}^2}$$

$$\sigma_B = \sqrt{\frac{1}{J}\sum_{j=1}^{J} \{B(j)-m_B\}^2}$$

C: Cross correlation coefficient

Figure 22A:
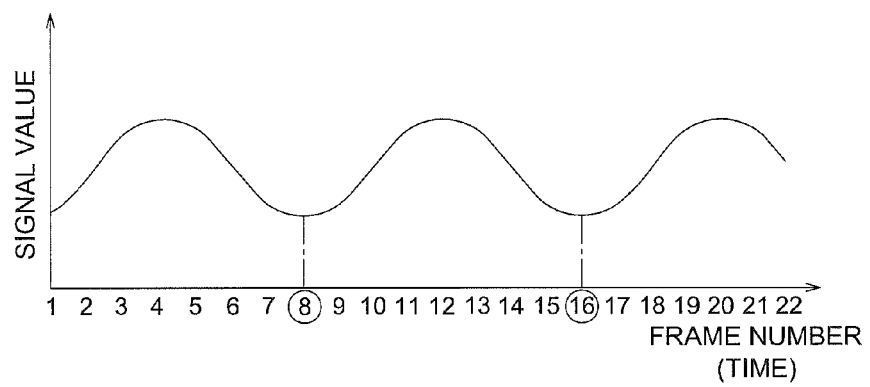
FIGS. 22A and 22B are figures for explaining a calculation method of a cross correlation coefficient.
Figure 22B:
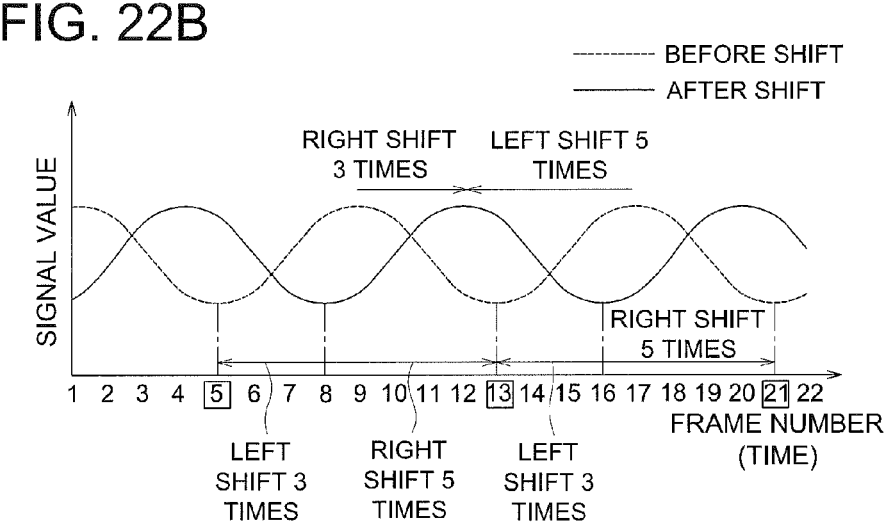

A (j): Signal value of the j-th of all the signals J included in the pulsation signal waveform $m_A$: Average signal value of all the signals included in the pulsation signal waveform $\sigma_A$: Standard deviation of all the signals included in the pulsation signal waveform B (j): Signal value of the j-th of all the signals J included in the output waveform of small area $m_B$: Average signal value of all the signals included in the output waveform of small area $\sigma_B$: Standard deviation of all the signals included in the output waveform of small area The number of the frame image of the timing when the lung blood vessel is expanded by the blood flow is specified for each small area based on the shifted quantity (shift amount) when the cross correlation coefficient becomes the maximum (Step S208). For example, when the output signal waveform of a certain small area is the output signal waveform shown in FIG. 22B by the dotted line to the pulsation signal waveform whose one cardiac beat cycle shown in FIG. 22A is about eight frames, the cross correlation coefficient becomes maximum when the output signal waveform shown in FIG. 22B is shifted to the left by the interval of time corresponding to five frames. Then, frame images of the numbers 13 and 21 to which the frames images of the numbers 8 and 16 of the timing when the heart contracts most in the pulsation signal waveform obtained at Step S206 were shifted five frames to the right are specified as the frame images of the timing when the lung blood vessel is expanded by the blood flow in the small area.

And, for each small area, for example, as identification information which shows the timing when the lung blood vessel is expanded by the blood flow, red color is assigned to the small area of the frame image of the frame number specified at Step S208, and black color is assigned to the small area of the other frame images (Step S209), and the frame image of the motion image in which red color and black color are assigned to each small area is displayed by motion image (displayed sequentially) on the display 34 (Step S210).

An example of the frame image group by which is displayed by motion image on the display 34 in Step S210 is shown in FIG. 23. In Step S210, the frame images are displayed sequentially, starting from the upper left of FIG. 23. As shown in FIG. 23, since the lung blood vessel of each small are is displayed by motion image in red color (it is gray in FIG. 23) at the timing when the lung blood vessel is expanded in a chronological order by the blood flow, the observer such as the doctor can recognize visually the image of the blood flow even if contrast agent is not used like before. And it becomes possible to diagnose whether the blood flow is normal or the blood flow is blocked at any portion. Since the feature amount is not calculated based on the difference between frames like the analysis relating to breathing, the accurate diagnostic support information according to each of the breathing and the blood flow can be offered without deteriorating the S/N ratio compared with the analysis result of the breathing like before.

Further, as the coloring display method, not only the frame of the timing when the lung blood vessel is expanded to the maximum by the blood flow is colored, but also the image colored according to the value of the cross correlation coefficient of each frame in each small area may be displayed. For example, the frame image of the motion image where strong red (red of high chroma) is applied to the frame with the high positive cross correlation coefficient value (frame of the neighborhood where the lung blood vessel is expanded to the maximum by the blood flow), weak red (red of low chroma) is applied to the frame with the positive low cross correlation coefficient (frame where the lung blood vessel is expanded somewhat by the blood flow), and the black color is applied to the frame with the negative cross correlation coefficient (frame where the blood flow does not exist in the lung blood vessel) is displayed by motion image (displaying sequentially) to the display 34. By performing such the display, the doctor can recognize visually not only the timing when the lung blood vessel is expanded to the maximum by the blood flow but also image in which blood flows through the lung blood vessel more smoothly.

In the above mentioned image analysis processing, although the blood flow signal can be extracted with sufficient accuracy by using the cross correlation coefficient of the pulsation signal waveform which shows the pulsation of the heart and the output signal waveform of each small area, the signal of the timing when the output signal waveform is the local minimum may be extracted as the signal which shows a blood flow, without using the cross correlation coefficient, according to the accuracy and processing speed which are required. For example, by calculating the cardiac beat cycle from the pulsation signal waveform, only the local minimum which appears at the interval of the cardiac beat cycle in the output signal waveform may be extracted as the signal which shows the blood flow. Further, the frame image colored at the blood vessel expansion timing may be changed not only to the motion image display but also to the parallel display. Further, although the cross correlation coefficient is calculated by using the pulsation signal waveform of the plural periods and the output signal waveform in the above description, it is also preferable to prepare the mode in which the pulsation signal waveform of one to 1.5 cardiac beats centering on the timing of the local minimum to the cardiac beats of each one cycle of the pulsation signal waveform is extracted, the output wave form is shifted to the left one frame by one frame and to the right if necessary to the each extracted pulsation signal waveform, as same as the case of the plural cycle periods, and the cross correlation coefficient is calculated. Thus, when noises such as abnormal heart rhythm are in a certain one cycle, it becomes easily influenced by dividing the pulsation signal waveform for each cardiac beat, but the timing of blood vessel expansion of each small area within the lung field can be calculated more correctly for each one cardiac beat. Further, in addition to this, as the image which expresses the relative delay degree of the output signal waveform of each small area within the lung field to the pulsation of the heart, the colored image is generated by simply corresponding with the cross correlation coefficient of the pulsation signal waveform of the plural cycle periods and the output signal waveform with colors (luminosity, chroma saturation, brightness, hue, and so on), and the image generated while the output signal waveform is shifted one frame by one frame may be displayed by motion image or may be displayed parallel. Thus, the image of which coloring is emphasized at the timing when the similarity with the pulsation signal waveform is high can be displayed by motion image or can be displayed parallel. Also in the display image, it is possible to observe the situation that the expansion of the lung blood vessel by the blood flow spreads in the lung field in a chronological order, as the relative delay on the basis of the pulsation signal waveform. Further, at this time, by calculating one representative value such as the maximum and the average value from the cross correlation coefficient to the plural shift amounts which are calculated by shifting the output signal waveform one frame by one frame, in each small area, the image which is displayed colored by corresponding the color to the calculated representative value may be generated and displayed. So, this makes it possible to display the similarity degree to the pulsation signal waveform of the output signal waveform in each small area as the blood flow information within the lung field in the form integrated in one image so that the doctor can recognize easily at a glance the similarity degree. Furthermore, when the color is displayed by corresponding the color with this cross correlation coefficient, by calculating the cross correlation coefficient without normalizing (without division) by $\sigma_B$ to "Equation 1", the value of this cross correlation coefficient becomes large corresponding not only to the similarity with the pulsation signal waveform but also with the size of the output signal waveform. Thus, by not performing normalization by $\sigma_B$, the image of which coloring is emphasized can be displayed by motion image or displayed parallel in the timing when the similarity with the pulsation signal waveform is high and in the small area where the amplitude of the output signal waveform is large. By enabling such the display, the doctor can judge the normality/abnormality of the patient, including not only at the blood vessel expansion timing of each small area within the lung field to the pulsation of the heart, but also including the degree of expansion of the blood vessel in each small area and can raise diagnostic accuracy.

Further, in order to increase the analysis accuracy, the configuration in which the radiograph with grid is taken or the offset compensation processing and gain compensation processing are performed may be employed.

2nd Embodiment

Next, the configuration of the 2nd embodiment of the invention is explained.

In the 2nd embodiment, the case of the application of this invention to the portable chest diagnostic support information generation system 70 for patients who are difficult to move is explained.

Figure 24:
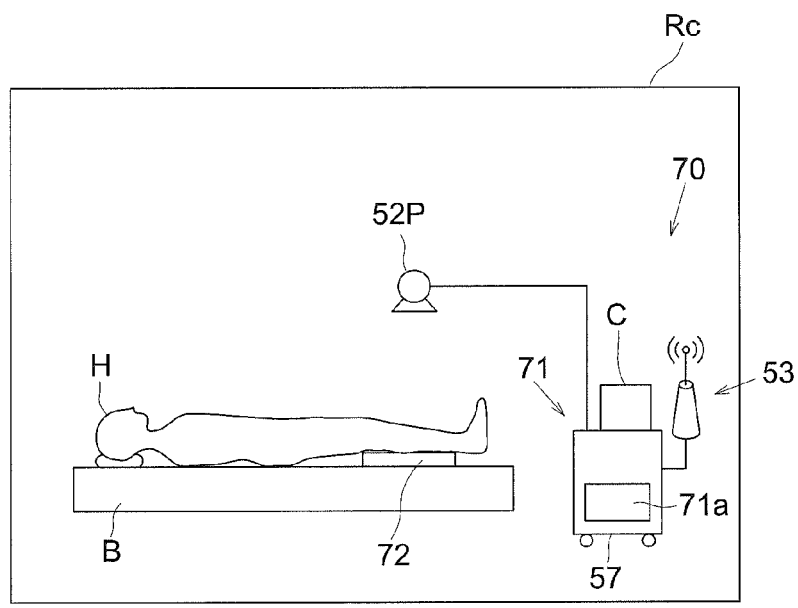
FIG. 24 is a figure showing an example of a whole configuration of a portable chest diagnostic support information generation system in the 2nd embodiment; and, FIG. 25 is a figure showing the example of functional configuration of FPD of FIG. 24.

As shown in FIG. 24, the portable chest diagnostic support information generation system 70 is a system which is carried into the patient room Rc and so on together with the round visiting car 71 and takes radiograph by irradiating radiation from the portable radiation source 52P in the state where the FPD cassette 72 is inserted between the body of the radiographic subject H which is lying down on Bed B, for example, to generate diagnostic support information.

As shown in FIG. 24, the portable chest diagnostic support information generation system 70 is provided with the portable radiation source 52P and the radiation generating equipment 57 carried on the visiting car 71. And the console C and the FPD cassette 72 are portable and can carry out wireless connection through an access point 53 which is provided on the visiting car 71.

The basic configuration of console C is a configuration equipped with a control section, a memory, a operation section, a display, and the communication section like the console for radiography 2 or the console for diagnosis 3.

The program for displaying the image data (still image or motion image) transmitted from FPD (Flat Panel Detector) 72 which is a portable type radiation detector for the check of positioning and the program for performing image analysis processing explained in FIG. 5 are memorized in the memory of console C. Further, Console C is equipped with the connector for connecting with the FPD cassette 72 with a cable and so on, and performing data communications.

Although radiographers, such as a technologist, may bring the FPD cassette 72, the FPD cassette 72 is comparatively heavy and may break or becomes out of order if the FPD cassette 72 is dropped. Therefore, the FPD cassette 72 is inserted in a pocket 71a prepared on the visiting car 71 and can be held and conveyed together with the visiting car 71.

The FPD cassette 72 is an FPD compatible with motion imaging and still imaging.

Figure 25:
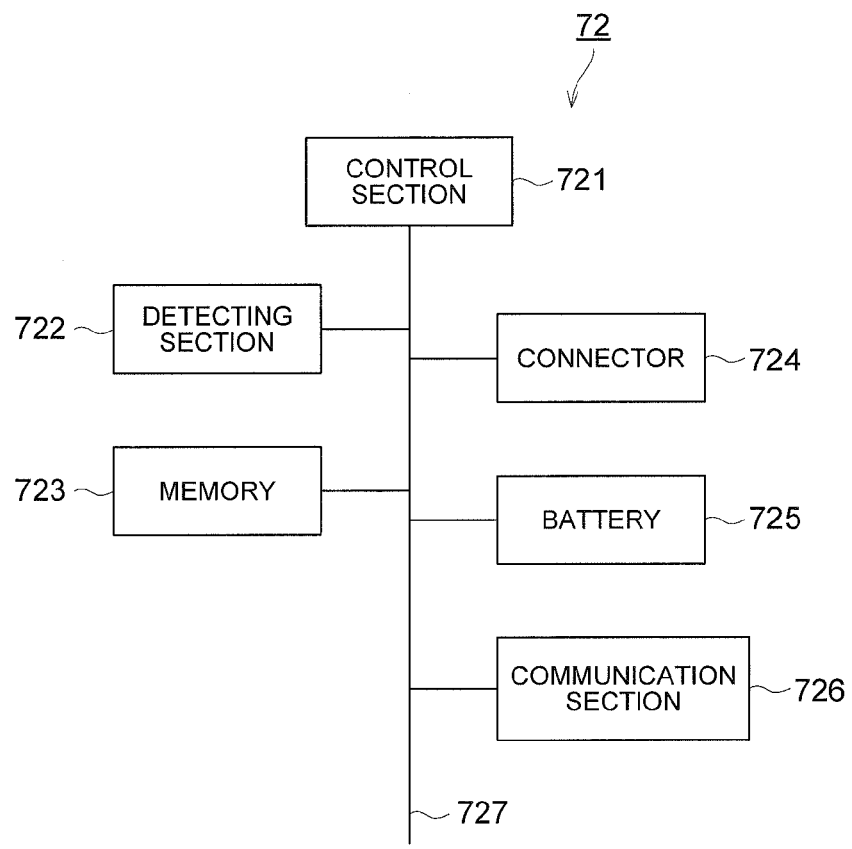

As shown in FIG. 25, this FPD cassette 72 is configured to have a control section 721, a detecting section 722, a memory 723, a connector 724, a battery 725, a radio communication section 726 and so on, and each part is connected by bus 727.

The control section 721 is configured by CPU, RAM, and so on

The CPU of the control section 721 reads various programs memorized in the memory 723, such as a system program and a processing program, and develops them to the RAM, and performs various processings according to the developed program.

For example, when the control section 721 is connected with console C through the connector 724 with the cable, the control section 721 will be shifted to motion imaging mode, and will be changed into the configuration of the power supply through the connector 724 with the cable, and carry out cable communications instead of wireless communications. That is for not giving noises to other frame images during transmission of obtained frame image, for shortening the transfer time itself, and for preventing the battery from being run out in the middle of the series of motion imaging, since the generated data capacity and the transfer time thereof in motion imaging increase compared with still imaging. And the control section 721 performs the processing of motion imaging mode. Namely, the control section 721 controls the switching part of the detecting section 722 based on the image reading condition for motion imaging memorized in the memory 723, so that by switching the reading of the electric signal accumulated in each detection element (pixel), and image data (frame image) is generated by reading the electric signal accumulated in the detecting section 722. Subsequently, the lung field area of the generated frame image is divided into small plural areas, and binning processing which transposes the output signal value of each small area of each frame to the representative values (average value, median, mode, and so on) of the each small area is performed. And the image data of the frame image carried out binning processing is transmitted to the console C through the connector 724 sequentially.

On the other hand, when it is judged that the control section 721 does not connect with console C through the connector 724, the control section 721 performs the processing of still imaging mode. Namely, the automatic detection for start of radiation by the detecting section 722 is enabled, and the switching part of the detecting section 722 is controlled based on the image reading condition for still imaging memorized in the memory 723 so that by switching reading of the electric signal accumulated in each detection element, image data (still image) is generated by reading the electric signal accumulated in the detecting section 722. And the image data of the generated still image is transmitted to the console C through the radio communication section 726 (wireless communication).

The detecting section 722 has a glass substrate and so on, for example, and plural detection elements which detect the radiation irradiated from the radiation source 52P and penetrating at least the radiographic subject according to the intensity, change the detected radiation into electric signal and accumulate the electric signal are arranged in the shape of two dimension on a predetermined position on the substrate irradiated. Each detection element is constituted by a semiconductor image sensor such as a photo diode and is connected to a switching part such as TFT (Thin Film Transistor), for example, and the accumulation and read out of electric signal of the each detection element is controlled by the switching part. Each output of the detection elements (pixels) which constitutes the generated still image or frame image represents the signal value (here density value).

The memory 723 is configured by nonvolatile memory of semiconductor and so on, for example. Various programs for controlling the detecting section 722, the image reading condition for motion imaging and still imaging and so on are memorized in the memory 723. Further, the image data output from the detecting section 722 is temporarily memorized in the memory 723.

The connector 724 can be connected with the connector at the side of console C through the cable, and performs data transmission and reception with console C.

Further, the connector 724 supplies the electric power supplied from console C to each functional part. In addition, it may be configured to charge the battery 725.

The battery 725 supplies electric power to each part of the FPD cassette 72 based on the control of the control section 721. As the battery 725, a nickel-cadmium battery, a nickel hydride battery, a lithium ion battery, and so on which are rechargeable can be used.

The Radio Communication section 726 performs data communications with console C by radio (wireless) through the access point 53. With this embodiment, identification information (namely, SSID) different from any of identification information (SSID) assigned to other access points is assigned to the access point 53 in the portable chest diagnostic support information generation system 70. Therefore, the access point 53 of the portable chest diagnostic support information generation system 70 transmits image data and so on only transmitted from the FPD cassette 72 to which the SSID of the access point 53 has been set up, to the console C, and does not accept any image data received from the FPD cassette to which other SSID(s) has been set up. Therefore, it becomes possible to prevent surely interference of signals arising between the portable chest diagnostic support information generation system 70 and other systems.

Hereafter the operation at the time of the motion imaging in the portable chest diagnostic support information generation system 70 is explained.

In the FPD cassette 72, when the connector of console C is connected to the connector 724 through the cable, the imaging mode is switched to the motion imaging mode, and the motion imaging will be performed. At this time, in order to reduce the amount of the radiation dose to the patient and avoid the obstacle of positioning, it is preferable to take radiograph without grid. The image data of the frame image generated by radiography is subject to the binning processing, by dividing the lung field area of each frame image into the small area (block), and is transmitted to console C through the connector 724. It is desirable to be capable of checking positioning on or near real time, since, in many cases, the radiographic subject H is a critical patient for the radiography by round visit. Therefore, it is desirable to choose large size binning, for example, about 4 pixels×4 pixels, compared with the binning size (for example, 2 pixels×2 pixels) at the time of radiography in radiographing room to reduce transfer time.

When the plural frame images are received in the console C from the FPD cassette 72, while each received frame image is memorized in the memory, the output of each pixel of each frame image is thinned out to be displayed by the display sequentially for the check of positioning or the motion state cycle (for the preview). In the preview, each frame image without compensation (raw data of each frame image outputted by the detector) can be displayed at every time when the console received each frame image before memorizing. In this case, the radiographer can judge the positioning and/or the motion state cycle quickly. By the way, the frame image data received continuously by console C is treated as one series image (image of one motion imaging set). When there is no reception of image data in the time predetermined in advance, it is judged that the radiography of one set has completed, and the image is corresponded with the radiography order information memorized in advance.

In addition, it is also preferable to classify each frame image based on the expiration period or the inspiration period and display each classified group (the expiration frame image group and the inspiration frame image group) on the display, instead of displaying each frame image sequentially for the preview. For example, when the signal value of a pixel or a small area corresponding to the reference position of the lung field is larger than that of previous frame image, the frame image can be classified into the inspiration frame image group, and when it is small, the frame image can be classified into the expiration frame image group. By this way, when the radiography is less than one cycle of breathing, the radiographer can recognize easily that re-radiography is needed. Further, since the operation can be started immediately after next frame image arrives, it does not take so much processing time.

In the console C, when the direction that the re-radiography is no needed is input from the operation section, the image analysis processing of the type (breathing and/or blood flow) specified from the operation section will be performed, and the analysis result will be displayed on the display. The explanation about the flow of a concrete processing of the image analysis processing is the same as that of what was explained in theist embodiment, and is omitted here. Further, when the instant analysis result for the round trip is not needed on the spot, the image data may be transmit to the console (console for diagnosis 3 of the 1st embodiment) in the radiographing room to perform the image analysis processing.

According to the portable chest diagnostic support information generation system 70 in the 2nd embodiment, in the round visit also, it becomes possible to perform the analysis of breathing and blood flow efficiently by only one motion imaging with reducing the radiation dose As explained above, according to the chest diagnostic support information generation system 100, the control section 31 of the console for diagnosis 3 generates the diagnostic support information relating to breathing of the radiographed subject based on the difference between neighboring frame images over the motion images. In calculating the difference, the control section 31 divides the radiation detector into plural blocks (above mentioned small area) using a certain frame image among plural frame images and calculates difference value between neighboring frame images in each block. Further, the control section 31 generates the output signal waveform which shows the change of the signal values of the above mentioned pixel or block corresponded with each other, and generates the diagnostic support information relating to blood flow of the subject M based on the generated output signal waveform.

That is, by using the series of the plural frame images obtained by the motion imaging of only one time, the diagnostic support information is generated through calculating the feature amount based on the difference value between frames for breathing, and through the extraction of the blood-flow signal based on the output signal waveform for blood flow. Namely the diagnostic support information is generated by different methods for breathing and for blood flow.

Therefore, it becomes possible to provide accurate diagnostic support information for each of breathing and blood flow, without increasing the radiation dose of the patient because it is not necessary to radiograph respectively for the breathing analysis and for blood flow analysis, Further, since the still image is displayed when the diagnostic support information relating to breathing of the radiographic subject M which is the feature amount of the breathing function is displayed, and the motion image is displayed when the diagnostic support information relating to blood flow of the radiographic subject M which is the blood-flow signal of each small area is displayed, information required for diagnosis can be output in such a manner that the doctor easily recognizes, according to the content of the analysis support information.

Further, when the diagnostic support information relating to blood flow is generated, the cross correlation coefficient is calculated by shifting the output signal waveform by frame unit for each small area for the pulsation signal waveform of the heart when the motion imaging is carried out, the timing when the cross correlation coefficient becomes the maximum from the timing when the heart of which the pulsation signal waveform is obtained is contracted is specified as the timing when the lung blood vessel of the small area is expanded by the blood flow, and the identification information (here red color) which shows the timing when the lung vessel is expanded by the blood flow is given to the small area of the frame image of the specified timing. Therefore, even in the case when an abnormality, such as abnormal heart rhythm, may exist, the timing which the lung blood vessel of each small area is expanded by the blood flow can be specified accurately.

Further, since the calculation of the cross correlation coefficient is performed using the pulsation signal waveform and the output signal waveform of plural cycle periods, it becomes possible to obtain the stable calculation result about the cross correlation coefficient even in the case when the abnormality, such as abnormal heart rhythm, may exist in a certain one cycle.

Further, since the offset compensation processing, gain compensation processing, and defective pixel compensation processing are not always needed when generating the diagnostic support information relating to the motion state of the radiography subject, the processing time involved in the generation of the diagnostic support information relating to the motion state can be reduced.

Further, since the radiography is taken without grid in generating the diagnostic support information relating to the motion state of the radiographic subject, the radiation dose to the radiographic subject M can be reduced while the amount of radiation reaching to the radiation detector 13 is maintained almost same as the previous.

Even in the portable chest diagnostic support information generation system 70, the same effective result as the abovementioned chest diagnostic support information generation system can be achieved.

In addition, the descriptive content of the above 1st and the 2nd embodiments is of relating a preferable example of this invention, and the invention is not limited to these embodiments.

Further, the detail configurations of each device and detail operations which constitute the chest diagnostic support information generation system 100 and the portable chest diagnostic support information generation system 70 also can be modified suitably in the range which does not deviate from the meaning of the invention.

What is claimed is:

1. A chest diagnostic support information generation system comprising:
a radiography section which radiographs a chest portion of a subject by using a radiation source and a radiation detector which generates an image data of the subject by detecting by a plurality of detection elements arranged two dimensionally, radiation having penetrated through the subject which is irradiated from the radiation source;
an image analysis section which generates a diagnostic support information relating to the chest portion of the subject based on the image data generated by the radiography section; and
a display which displays the diagnostic support information generated by the image analysis section,
wherein the radiography section is structured to obtain a plurality of frame images which show a motion state of the chest of the subject by irradiating radiation continuously from the radiation source, and the image analysis section comprises:
a breathing information generation section which, for the plurality of frame images obtained by the radiography section, corresponds a pixel or a block from each of the plurality of frame images with each other, wherein the pixel or block from each of the plurality of frame images represents signal values output by a detection element of a same position in the radiation detector among the plurality of image frames, and the breathing information generation section generates the diagnostic support information relating to breathing of the subject based on a difference value of the pixel or the block corresponded with each other between image frames temporally adjacent; and
a blood flow information generation section which, for the plurality of frame images obtained by the radiography section, corresponds a pixel or a block from each of the plurality of frame images with each other, wherein the pixel or block from each of the plurality of frame images represents signal values output by the detection element of the same position in the radiation detector among the plurality of image frames, and the blood flow information generation section generates an output signal wave form which represents a temporal change of signal values of the pixel or the block corresponded with each other, and generates the diagnostic support information relating to blood flow of the subject based on the generated output signal wave form.

2. The chest diagnostic support information generation system described in claim 1, wherein the breathing information generation section extracts a lung field area from at least one of the plurality of frame images, calculates a difference value of signal values between neighboring frame images for each pixel or each block corresponding to the extracted lung field area, and generates a feature amount relating to breathing at the pixel or the each block based on the calculated difference value as the diagnostic support information relating to breathing of the subject, and
the blood flow information generation section extracts a lung field area from at least one of the plurality of frame images, specifies a frame image of a timing when a lung blood vessel of the pixels or blocks is expanded by the blood flow by analyzing the output signal wave form for the each pixel or the each block, and generates the diagnostic support information relating to blood flow of the subject by giving an identification information indicating the timing of expansion of lung vessels by the blood flow to the pixel or block of the specified frame image.

3. The chest diagnostic support information generation system described in claim 2, wherein the display displays a still image when displaying the diagnostic support information relating to breathing of the subject, and displays a motion image when displaying the diagnostic support information relating to blood flow of the subject.

4. The chest diagnostic support information generation system described in claim 1, further comprising a pulsation signal waveform obtaining section to obtain a pulsation signal waveform which shows a pulsation of the heart of the subject in a radiography period of the plurality of frame images,
wherein the blood flow information generation section generates the output signal waveform of the pixel or the block by plotting a point corresponding to the signal value of the pixel or the block of the each frame image on a coordinate plane where a horizontal axis represents frame numbers which show an order of radiography of frame images and a vertical axis represents the signal values of the pixel or the block for the pixel or the block, calculates a cross correlation coefficient between the pulsation signal waveform and the output signal waveform by shifting the output signal waveform respecting to the obtained pulsation signal waveform by frame number unit, and specifies the frame image of a timing of a shift amount when the cross correlation coefficient becomes a maximum from a timing when the heart contracted most in the pulsation signal waveform as the frame image of the timing when the lung blood vessel is expanded by the blood flow at the pixel or the block.

5. The chest diagnostic support information generation system described in claim 4, wherein the pulsation signal waveform obtaining section is any one of an electrocardiographic sensor which obtains a cardiac electric wave form, a section obtaining a waveform which shows a temporal change of the signal value in a heart region or the main artery area from the plurality of frame images as the pulsation signal waveform, and a section obtaining the waveform which, by extracting a heart wall position from the plurality of frame images, shows a temporal change of the extracted heart wall position as a pulsation signal.

6. The chest diagnostic support information generation system described in claim 1, wherein the blood flow information generation section obtains the information relating to the blood flow by using the output signal wave form and the pulsation signal waveform of a plurality of cycle periods.

7. The chest diagnostic support information generation system described in claim 1, further comprising:
   a compensation section to carry out at least one of an offset compensation processing and a gain compensation processing to the image data obtained by the radiography section; and
   a control section which performs a control whether or not the compensation by the compensation section is carried out to the image data obtained by the radiography section,
   wherein the control section perform a control not to carry out the compensation by the compensation section when the diagnostic support information relating to the motion state of the subject is generated by the image analysis section.

8. The chest diagnostic support information generation system described in claim 1, further comprising:
   a scattered radiation removal grid which removes a dispersion radiation from the radiation source; and
   a radiography control section which controls whether or not the radiography is performed by using the scattered radiation removal grid,
   wherein the radiography control section controls so that the radiography is performed without the scattered radiation removal grid when the image analysis section generates the diagnostic support information relating to the motion state of the subject.

9. The chest diagnostic support information generation system described in claim 1, wherein, regarding the corresponding, one frame image among the plurality of frame images obtained by the radiography section is set as a standard image,
   at least a portion of the standard image is divided into a plurality of small areas,
   other frame images among the plurality of frame images are divided into small areas with same pixel positions as the small areas of the standard image, and
   the small areas with the same pixel position among the frame images are corresponded to each other.

10. The chest diagnostic support information generation system described in claim 9, wherein the standard image is a frame image of a quiet expiration state.

\* \* \* \* \*